United States Patent
Rondeau

(10) Patent No.: US 6,432,146 B1
(45) Date of Patent: Aug. 13, 2002

(54) USE OF A COMBINATION OF TWO CATIONIC DYES FOR THE DIRECT DYEING OF KERATIN FIBERS

(75) Inventor: Christine Rondeau, Sartrouville (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/487,665

(22) Filed: Jan. 19, 2000

(30) Foreign Application Priority Data

Jan. 19, 1999 (FR) .............................. 99 00501

(51) Int. Cl.$^7$ ................................. A61K 7/13
(52) U.S. Cl. ................. 8/407; 8/407; 8/405; 8/408; 8/409; 8/410; 8/411; 8/423; 8/426
(58) Field of Search ............................ 8/405, 407, 411, 8/408, 409, 410, 423, 426

(56) References Cited

U.S. PATENT DOCUMENTS

| | | | |
|---|---|---|---|
| 3,869,454 A | 3/1975 | Lang et al. | 260/244 R |
| 3,955,918 A | 5/1976 | Lang | 8/41 |
| 3,985,499 A | 10/1976 | Lang et al. | 8/10.1 |
| 4,151,162 A | 4/1979 | Lang et al. | 260/158 |
| 4,153,065 A | 5/1979 | Lang | 132/7 |
| 5,879,412 A | * 3/1999 | Rondeau et al. | 8/411 |
| 5,993,490 A | * 11/1999 | Rondeau et al. | 8/409 |
| 6,001,135 A | * 12/1999 | Rondeau et al. | 8/407 |
| 6,190,421 B1 | * 2/2001 | Rondeau et al. | 8/407 |

FOREIGN PATENT DOCUMENTS

| | | |
|---|---|---|
| EP | 0 714 954 | 6/1996 |
| EP | 0 850 638 | 7/1998 |
| EP | 0 962 220 | 12/1999 |
| FR | 2 140 205 | 1/1973 |
| FR | 2 189 006 | 1/1974 |
| FR | 2 285 851 | 4/1976 |
| FR | 2 757 387 | 6/1998 |
| GB | 2 057 019 | 3/1981 |
| WO | WO 95/01772 | 1/1995 |
| WO | WO 95/15144 | 6/1995 |
| WO | WO 97/39727 | 10/1997 |
| WO | WO 99/20234 | 4/1999 |

OTHER PUBLICATIONS

English language Derwent Abstract of EP 0 714 954, Jun. 1996.

English language Derwent Abstract of EP 0 850 638, Jul. 1998.

English language Derwent Abstract of FR 2 285 851, Apr. 1976.

\* cited by examiner

Primary Examiner—Lorna M. Douyon
Assistant Examiner—Eisa Elhilo
(74) Attorney, Agent, or Firm—Finnegan, Henderson, Farabow, Garrett & Dunner, L.L.P.

(57) ABSTRACT

The invention relates to dyeing compositions comprising a combination of two specific cationic dyes and not containing a self-oxidizing agent, to the use of the compositions as direct dyes in dyeing applications for keratin fibers, and in particular human keratin fibers such as the hair, to direct dyeing processes using the compositions, and to dyeing devices using the compositions.

52 Claims, No Drawings

USE OF A COMBINATION OF TWO CATIONIC DYES FOR THE DIRECT DYEING OF KERATIN FIBERS

The present invention relates to dyeing compositions comprising a combination of two specific cationic dyes and not containing a self-oxidizing agent, to the use of the compositions as direct dyes in dyeing applications for keratin fibers, and in particular human keratin fibers such as the hair, to direct dyeing processes using the compositions, and to dyeing devices using the compositions.

Two types of dyeing can be distinguished in the hair field.

The first is permanent dyeing or oxidation dyeing, which uses oxidation dyes that develop their dyeing power in the presence of oxidizing agents.

The second is semi-permanent or temporary dyeing, or direct dyeing, which uses dyes capable of giving the hair's natural color a more or less pronounced color change which may be able to withstand shampooing several times. These dyes are referred to as direct dyes; they can be used with or without an oxidizing agent. In the presence of an oxidizing agent, the dyeing is referred to as lightening; without an oxidizing agent, the dyeing is referred to as conventional direct dyeing rather than lightening dyeing.

The present invention relates to conventional direct dyeing, i.e., dyeing without an oxidizing agent, which is less aggressive towards keratin fibers.

Among the cationic direct dyes available for dyeing keratin fibers, in particular human keratin fibers, the compounds of formulae (I) to (III) defined below are already known. However, these dyes, generally referred to as Arianor dyes, give dyeing results which have properties that are insufficient with regard to the intensity and chromaticity of the shades obtained, the homogeneity of the color distributed along the fiber (the dyeing is then said to be too selective), and the staying power in terms of fastness with respect to the various attacking factors to which the hair may be subjected (e.g., light, bad weather, shampooing).

The inventor has just discovered, entirely surprisingly and unexpectedly, that a combination of at least one cationic dye of formulae (I) to (III) defined below and of at least one cationic dye of formulae (IV) to (VII) defined below is suitable for direct dyeing, and that, in addition, it makes it possible to obtain dye compositions which give relatively unselective and highly chromatic dyeing results that are particularly fast with respect to the various attacking factors to which the hair may be subjected.

This discovery forms the basis of the present invention.

A first subject of the present invention is thus the use, as a direct dye in, or for the manufacture of, direct dyeing compositions for keratin fibers and in particular for human keratin fibers such as the hair, of a combination comprising (i) at least one cationic dye of formulae (I) to (III) defined below, and (ii) at least one cationic dye of formulae (IV) to (VII) defined below, it being understood that the direct dyeing compositions do not contain a self-oxidizing dye:

(i) cationic dye of formulae (I), (II) and (III):

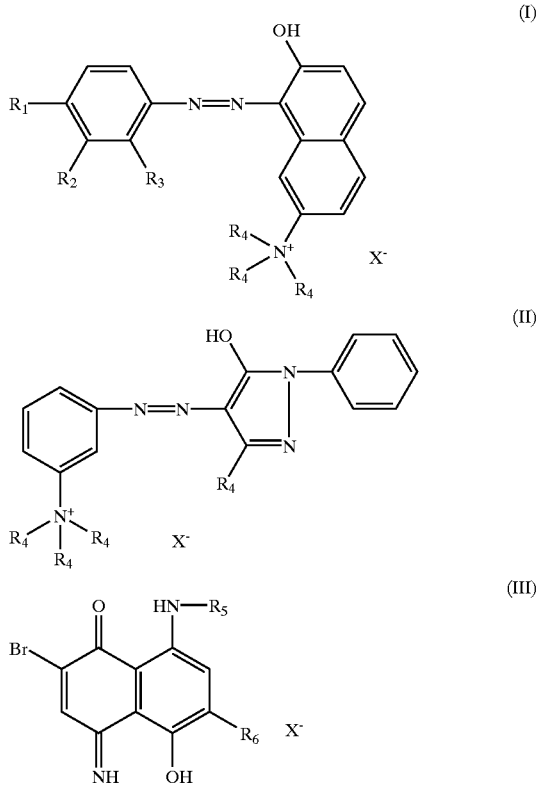

in which:

$R_1$ represents a hydrogen atom or an amino radical;

$R_2$ represents a hydrogen atom or a nitro group;

$R_3$ represents a hydrogen atom, a nitro group or a $C_1$–$C_4$ alkoxy radical;

$R_4$ represents a $C_1$–$C_4$ alkyl radical;

$R_5$ represents a hydrogen atom or a para-tri($C_1$–$C_4$) alkylammoniophenyl group;

$R_6$ represents a bromine atom or an NH-para-tri-($C_1$–$C_4$) alkylammoniophenyl group; and $X^-$ represents an anion preferably chosen from chloride, methylsulphate and acetate.

According to the present invention, the compounds corresponding to the mesomeric forms of structures (I) to (III) can also be used.

As examples of compounds of formula (I), mention may be made of the dyes Basic Brown 16, Basic Red 76, Basic Brown 17 and Basic Red 118.

As an example of compounds of formula (II), mention may be made of the dye Basic Yellow 57.

As an example of compounds of formula (III), mention may be made of the dye Basic Blue 99.

These Color Index names cover the following chemical structures (in the form of their chlorides):

8-((4-aminophenyl)azo)-7-hydroxy-2-trimethylammonionaphthalene, 8-((2-methoxyphenyl)azo)-7-hydroxy-2-trimethylammonionaphthalene, 8-((4-amino nitrophenyl)azo)-7-hydroxy-2-trimethylammonionaphthalene, 8-((4-amino-2-nitrophenyl)azo)-7-hydroxy-2-trimethylammonionaphthalene, 3-((3-methyl-5-hydroxy-1-phenyl-1H-pyrazol-4-yl)azo) trimethylammoniobenzene, 3-((4-amino-6-bromo-5,8-dihydro-1-hydroxy-8-imino-5-oxo-2-naphthyl)amino)trimethylammoniobenzene, and 3-((3,7-dibromo-5,8-dihydro-4-hydroxy-5-imino-8-oxo-1-naphthyl)amino)trimethylammoniobenzene.

The compounds of formulae (I) to (III) are found, alone or in combination, in the products corresponding to the trade names, sold by the company Warner Jenkinson: Arianor Mahogany, Arianor Steel Blue, Arianor Madder Red, Arianor Sienna Brown, Arianor Straw Yellow and Arianor Bordeaux.

(ii) cationic dye of formulae (IV), (V), (VI), (VI') and (VII) below:

a) compounds of formula (IV):

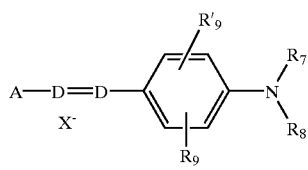

(IV)

in which:

D represents a nitrogen atom or a —CH group, $R_7$ and $R_8$, which may be identical or different, represent a hydrogen atom; a 4'-aminophenyl radical; or a $C_1$–$C_4$ alkyl radical which can be substituted with a —CN, —OH or —NH$_2$ radical, or which can form, with the nitrogen atom to which it is attached and with a carbon atom of the benzene ring, a heterocycle optionally comprising oxygen or additional nitrogen atoms and which can be substituted with one or more $C_1$–$C_4$ alkyl radicals;

$R_9$ and $R'_9$, which may be identical or different, represent a hydrogen atom, a halogen atom chosen from chlorine, bromine, iodine and fluorine, or a cyano, $C_1$–$C_4$ alkyl, $C_1$–$C_4$ alkoxy or acetyloxy radical;

X⁻ represents an anion preferably chosen from chloride, methylsulphate and acetate; and A represents a group chosen from the structures A1 to A19 below:

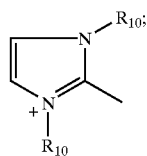

A₁

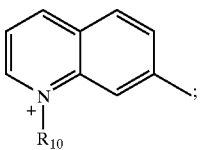

A₂

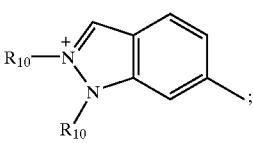

A₃

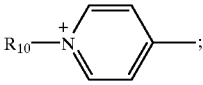

A₄

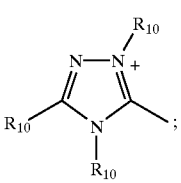

A₅

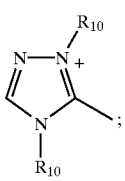

A₆

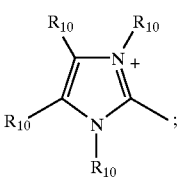

A₇

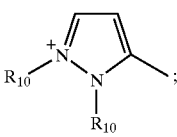

A₈

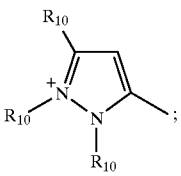

A₉

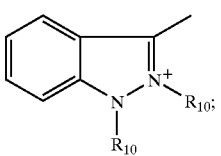

A₁₀

A11 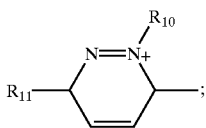

A12 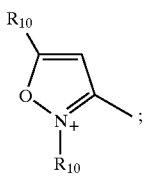

A13 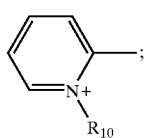

A14 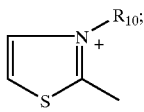

A15 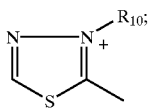

A16 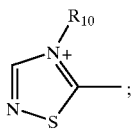

A17 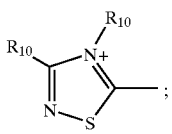

A18 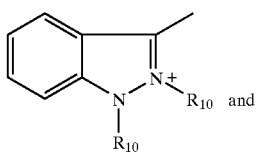

A19 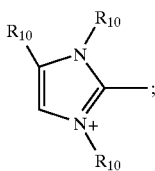

in which:

$R_{10}$ represents a $C_1$–$C_4$ alkyl radical which can be substituted with a hydroxyl radical; and $R_{11}$ represents a $C_1$–$C_4$ alkoxy radical;

with the provisos that:

(i) when D represents —CH, and A represents $A_4$ or $A_{13}$, and $R_9$ is other than an alkoxy radical, then $R_7$ and $R_8$ do not simultaneously denote a hydrogen atom; and (ii) when D represents a nitrogen atom, and A represents $A_6$, then $R_7$ and $R_8$ do not simultaneously denote a methyl radical.

b) compounds of formula (V):

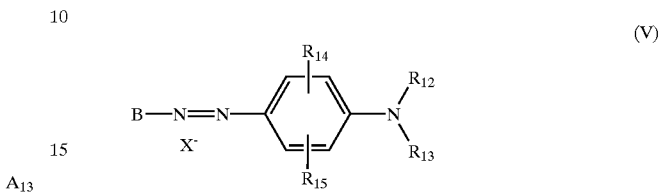

(V)

in which:

$R_{12}$ represents a hydrogen atom or a $C_1$–$C_4$ alkyl radical;

$R_{13}$ represents a hydrogen atom, an alkyl radical which can be substituted with a —CN radical or with an amino group, or a 4'-aminophenyl radical; or $R_{13}$ forms, together with $R_{12}$ and the nitrogen atom to which they are attached, a heterocycle optionally comprising oxygen and/or nitrogen, and which can be substituted with a $C_1$–$C_4$ alkyl radical;

$R_{14}$ and $R_{15}$, which may be identical or different, represent a hydrogen atom, a halogen atom such as bromine, chlorine, iodine and fluorine, a $C_1$–$C_4$ alkyl or $C_1$–$C_4$ alkoxy radical or a —CN radical;

$X^-$ represents an anion preferably chosen from chloride, methyl sulphate and acetate; and B represents a group chosen from the structures B1 to B6 below:

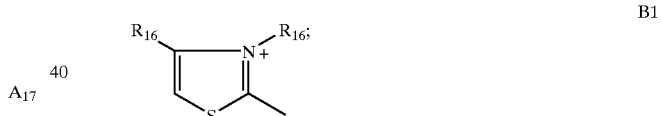

B1

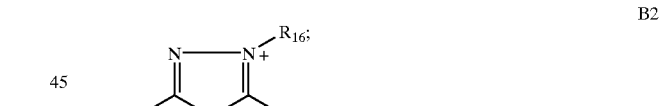

B2

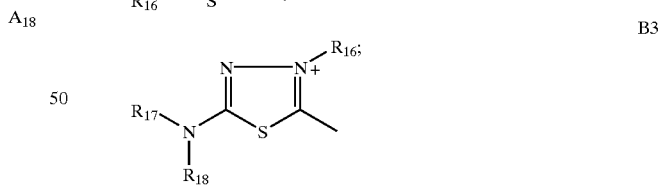

B3

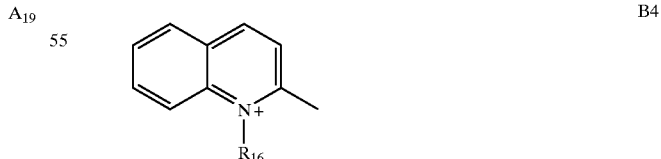

B4

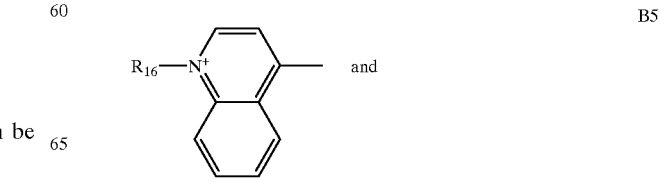

B5

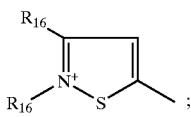
B6 in which:

$R_{16}$ represents a $C_1$–$C_4$ alkyl radical; and $R_{16}$ and $R_{17}$, which may be identical or different, represent a hydrogen atom or a $C_1$–$C_4$ alkyl radical;

(c) compounds of formulae (VI) and (VI'):

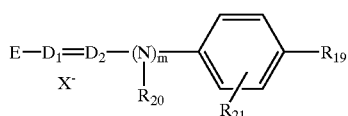
(VI)

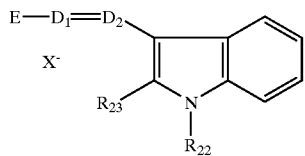
(VI')

in which:

$R_{19}$ represents a hydrogen atom, a $C_1$–$C_4$ alkoxy radical, a halogen atom such as bromine, chlorine, iodine and fluorine or an amino radical;

$R_{20}$ represents a hydrogen atom or a $C_1$–$C_4$ alkyl radical, or forms, with the nitrogen atom to which it is attached and a carbon atom of the benzene ring, a heterocycle optionally containing oxygen and/or substituted with one or more identical or different $C_1$–$C_4$ alkyl groups;

$R_{21}$ represents a hydrogen or halogen atom such as bromine, chlorine, iodine or fluorine;

$R_{22}$ and $R_{23}$, which may be identical or different, represent a hydrogen atom or a $C_1$–$C_4$ alkyl radical;

$D_1$ and $D_2$, which may be identical or different, represent a nitrogen atom or a —CH group;

m is equal to 0 or 1;

$X^-$ represents an anion preferably chosen from chloride, methyl sulphate and acetate; and E represents a group chosen from the structures E1 to E8 below:

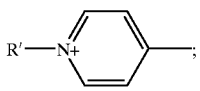
E1

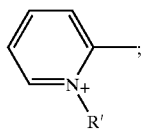
E2

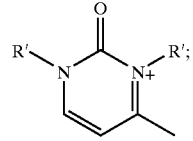
E3

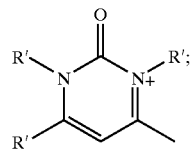
E4

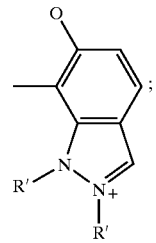
E5

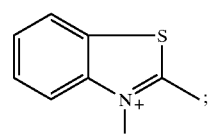
E6

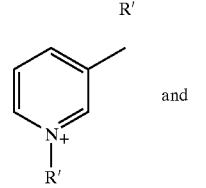
E7

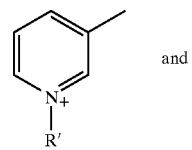
and

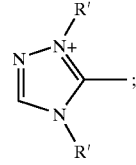
E8 in which R' represents a $C_1$–$C_4$ alkyl radical;

when m is equal to 0 and $D_1$ represents a nitrogen atom, then E can also denote a group of structure E9 below:

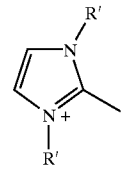
E9 in which R' represents a $C_1$–$C_4$ alkyl radical; it being understood that when $R_{19}$ represents an unsubstituted amino group, then $D_1$ and $D_2$ simultaneously represent a —CH group and m is equal to 0;

d) compounds of formula (VII):

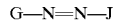
(VII)

in which:

G represents a group chosen from the structures $G_1$ to $G_3$ below:

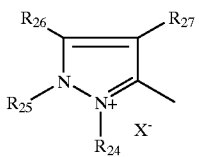

G₁

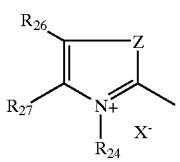

G₂

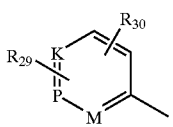

G₃ in which:
$R_{24}$ denotes a $C_1$–$C_4$ alkyl radical, a phenyl radical which can be substituted with a $C_1$–$C_4$ alkyl radical or a halogen atom chosen from chlorine, bromine, iodine and fluorine;

$R_{25}$ denotes a $C_1$–$C_4$ alkyl radical or a phenyl radical;

$R_{26}$ and $R_{27}$, which may be identical or different, represent a $C_1$–$C_4$ alkyl radical or a phenyl radical; or $R_{26}$ and $R_{27}$ together form, in $G_1$, a benzene ring substituted with one or more identical or different $C_1$–$C_4$ alkyl $C_1$–$C_4$ alkoxy or $NO_2$ radicals; or $R_{26}$ and $R_{27}$ together form, in $G_2$, a benzene ring optionally substituted with one or more identical or different $C_1$–$C_4$ alkyl, $C_1$–$C_4$ alkoxy or $NO_2$ radicals;

$R_{26}$ can also denote a hydrogen atom;

Z denotes an oxygen or sulphur atom or a group —$NR_{25}$;

M represents a —CH, —CR in which R denotes $C_1$–$C_4$ alkyl, or —$NR_{28}(X^-)_r$ group;

K represents a —CH, —CR in which R denotes $C_1$–$C_4$ alkyl, or —$NR_{28}(X^-)_r$ group;

P represents a —CH, —CR in which R denotes $C_1$–$C_4$ alkyl, or —$NR_{28}(X^-)_r$ group;

r denotes zero or 1;

$R_{28}$ represents an atom $O^-$, a $C_1$–$C_4$ alkoxy radical or a $C_1$–$C_4$ alkyl radical;

$R_{29}$ and $R_{30}$, which may be identical or different, represent a hydrogen atom, a halogen atom chosen from chlorine, bromine, iodine and fluorine, a $C_1$–$C_4$ alkyl or $C_1$–$C_4$ alkoxy radical or an —$NO_2$ radical;

$X^-$ represents an anion preferably chosen from chloride, iodide, methyl sulphate, ethyl sulphate, acetate and perchlorate;

with the proviso that:
if $R_{28}$ denotes $O^-$, then r denotes zero;
if K or P or M denotes $C_1$–$C_4$ —N-alkyl $X^-$, then $R_{29}$ or $R_{30}$ is other than a hydrogen atom;
if K denotes —$NR_{28}(X^-)_r$, then M=P and denotes —CH or —CR;
if M denotes —$NR_{28}(X^-)_r$, then K=P and denotes —CH or —CR;
if P denotes —$NR_{28}(X^-)_r$, then K=M and denotes —CH or —CR;
if Z denotes a sulphur atom and $R_{27}$ denotes $C_1$–$C_4$ alkyl, then $R_{26}$ is other than a hydrogen atom; and
if Z denotes —$NR_{28}$ and $R_{25}$ denotes $C_1$–$C_4$ alkyl, then at least one of the radicals $R_{24}$, $R_{26}$ or $R_{27}$ of $G_2$ is other than a $C_1$–$C_4$ alkyl radical;

J represents:
(a) a group of structure $J_1$ below:

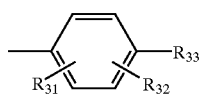

J₁ in which:
$R_{31}$ represents a hydrogen atom, a halogen atom chosen from chlorine, bromine, iodine and fluorine, a $C_1$–$C_4$ alkyl or $C_1$–$C_4$ alkoxy radical, or an —OH, —$NO_2$, —$NHR_{34}$, —$NR_{35}R_{36}$ or $C_1$–$C_4$—NHCO alkyl radical; or $R_{31}$ forms, together with $R_{32}$, a 5- or 6-membered ring optionally comprising one or more identical or different hetero atoms chosen from nitrogen, oxygen and sulphur;

$R_{32}$ represents a hydrogen atom, a halogen atom chosen from chlorine, bromine, iodine and fluorine, or a $C_1$–$C_4$ alkyl or $C_1$–$C_4$ alkoxy radical; or $R_{32}$ forms, with $R_{33}$ or $R_{34}$, a 5- or 6-membered ring optionally comprising one or more identical or different hetero atoms chosen from nitrogen, oxygen and sulphur;

$R_{33}$ represents a hydrogen atom, an —OH radical, an —$NHR_{34}$ radical or an —$NR_{35}R_{36}$ radical;

$R_{34}$ represents a hydrogen atom, a $C_1$–$C_4$ alkyl radical, a $C_1$–$C_4$ monohydroxyalkyl radical, a $C_2$–$C_4$ polyhydroxyalkyl radical or a phenyl radical;

$R_{35}$ and $R_{36}$, which may be identical or different, represent a $C_1$–$C_4$ alkyl radical, a $C_1$–$C_4$ monohydroxyalkyl radical or a $C_2$–$C_4$ polyhydroxyalkyl radical;

or
(b) a 5- or 6-membered nitrogenous heterocyclic group which can contain other hetero atoms and/or carbonyl groups and which can be substituted with one or more identical or different $C_1$–$C_4$ alkyl, amino or phenyl radicals, and in particular a group of structure $J_2$ below:

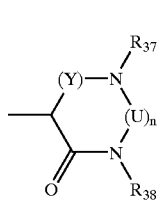

J₂ in which:
$R_{37}$ and $R_{38}$, which may be identical or different, represent a hydrogen atom, a $C_1$–$C_4$ alkyl radical or a phenyl radical;

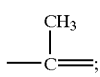

Y denotes a —CO-radical or a radical
n is equal to 0 or 1; and
U denotes a —CO— radical when n is equal to 1.

Compounds corresponding to the mesomeric forms of the structures (IV) to (VII) can also be used.

In the structures (IV) to (VII), as in the structures (I) to (III) defined above, the $C_1$–$C_4$ alkyl or alkoxy group preferably denotes methyl, ethyl, butyl, methoxy or ethoxy.

The cationic direct dyes of formulae (IV), (V), (VI) and (VI') which can be used in the dye compositions in accordance with the invention are known compounds and are described, for example, in patent applications WO 95/01772, WO 95/15144 and EP-A-0 714 954, the disclosures of which are incorporated by reference herein. The cationic direct dyes of formula (VII) which can be used in the dye compositions according to the invention are known compounds and are described, for example, in patent applications FR-2 189 006, FR-2 285 851 and FR-2 140 205 and the certificates of addition thereof, the disclosures of which are incorporated by reference herein.

Among the cationic direct dyes of formula (IV) which can be used in the dye compositions according to the invention, mention may be made more particularly of the compounds corresponding to the structures (IV1) to (IV54) below:

(IV1)
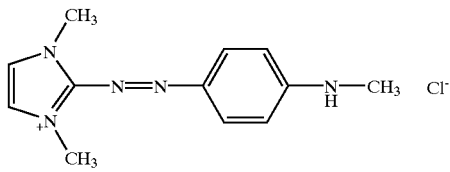

(IV2)
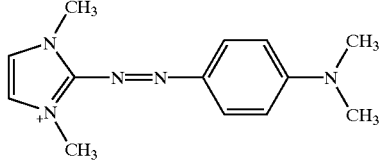

(IV3)
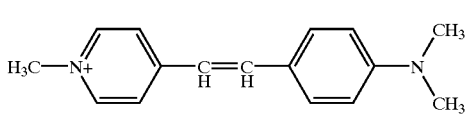

(IV4)
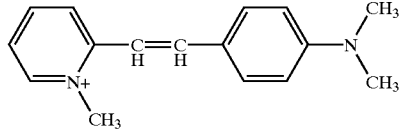

(IV5)
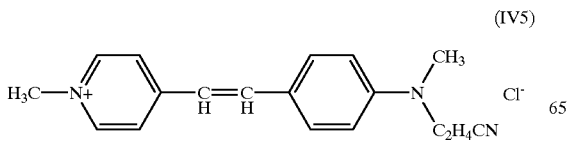

(IV6)
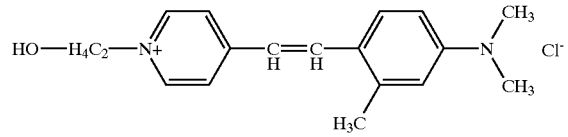

(IV7)
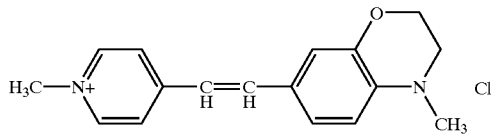

(IV8)
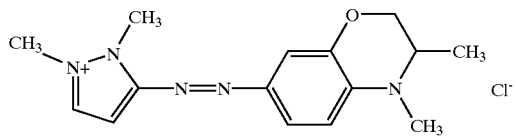

(IV9)
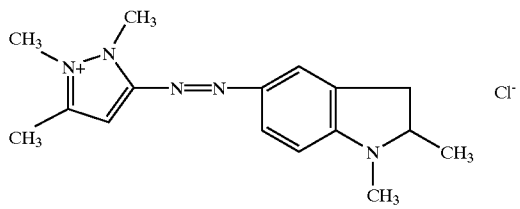

(IV10)
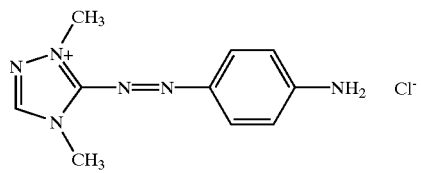

(IV11)
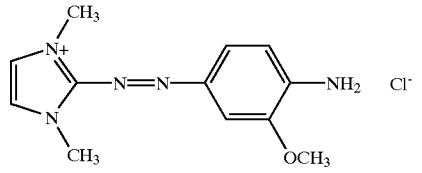

(IV12)
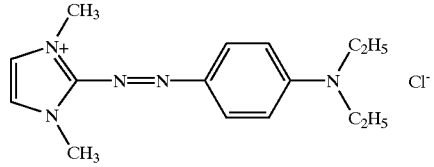

(IV13)
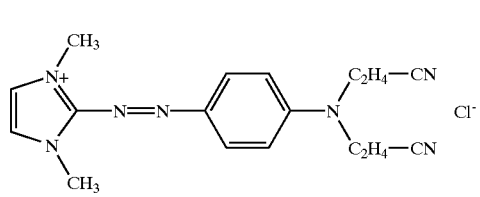

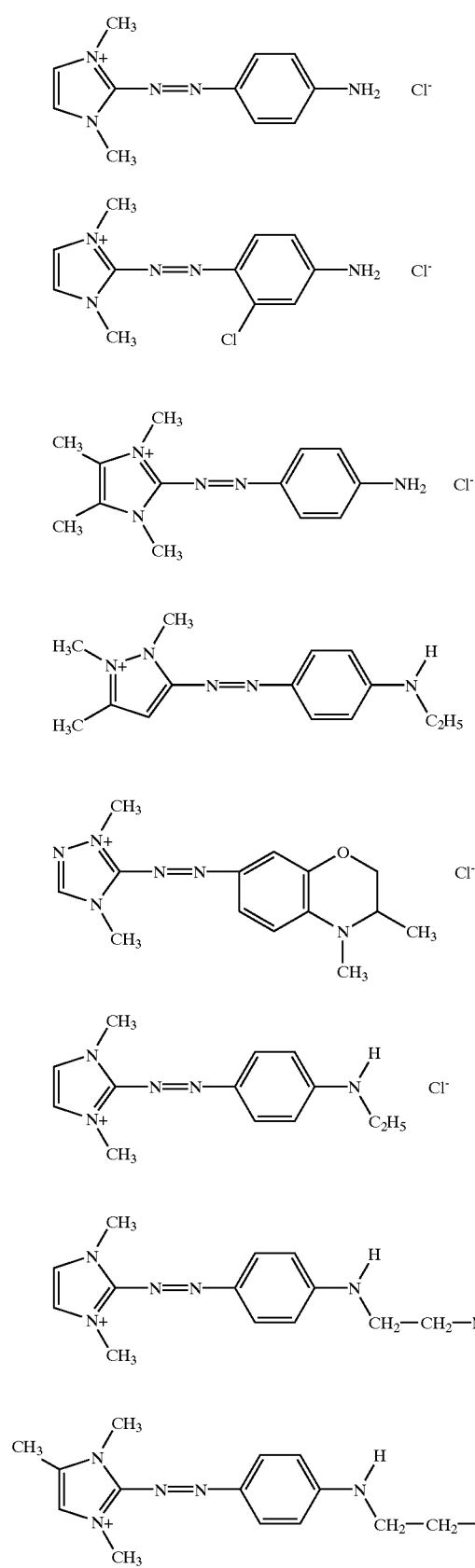
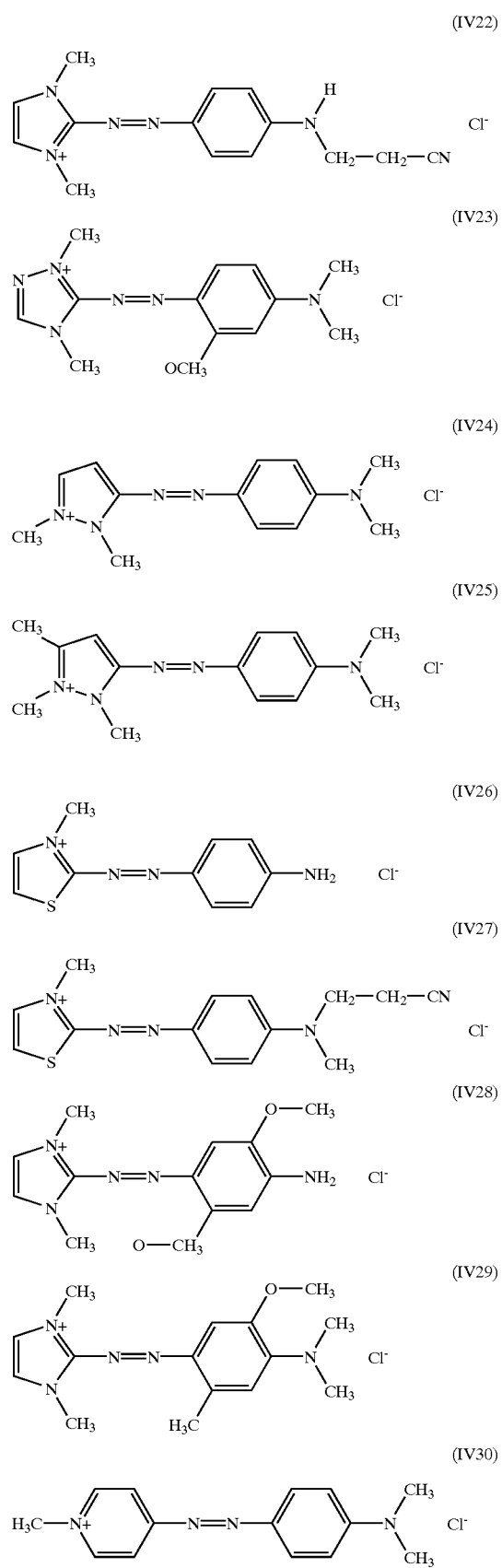

-continued (IV31), (IV32), (IV33), (IV34), (IV35), (IV36), (IV37), (IV38), (IV39), (IV40), (IV41), (IV42), (IV43), (IV44), (IV45), (IV46), (IV47)

-continued (IV48) 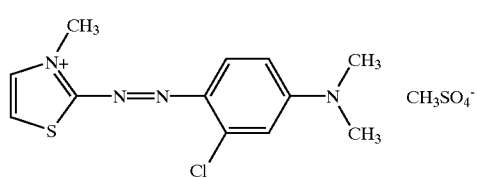

(IV49) 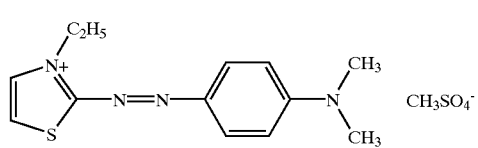

(IV50) 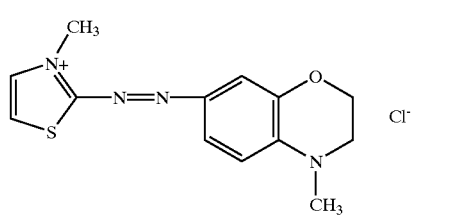

(IV51) 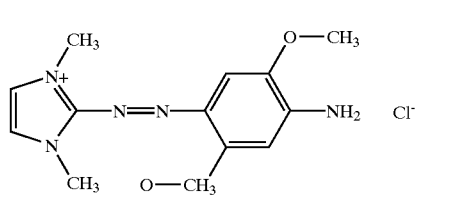

(IV52) 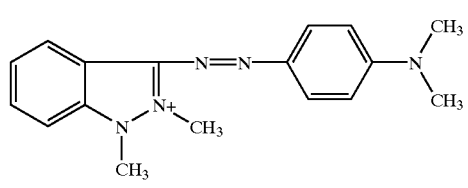

(IV53) 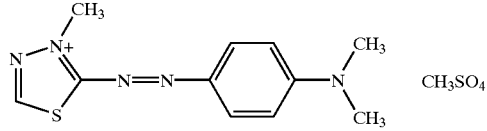

(IV54) 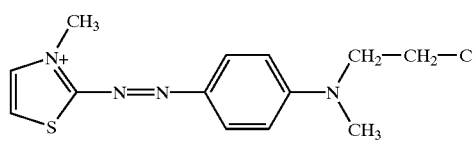

Among the compounds of the structures (IV1) to (IV54) described above, those most particularly preferred are the compounds corresponding to the structures (IV1), (IV2), (IV14) and (IV31).

Among the cationic direct dyes of formula (V) which can be used in the dye compositions according to the invention, mention may be made more particularly of the compounds corresponding to the structures (V1) to (V9) below:

(V1) 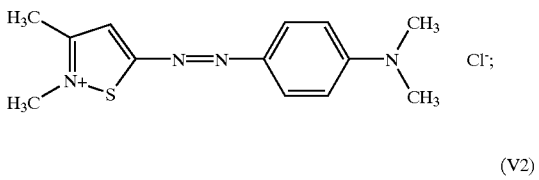

(V2) 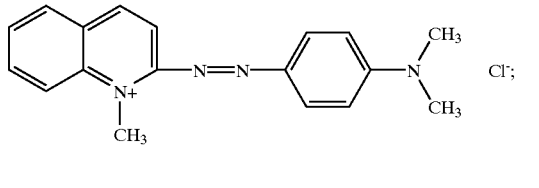

(V3) 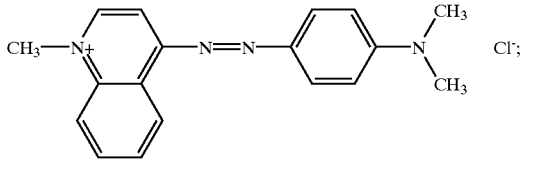

(V4) 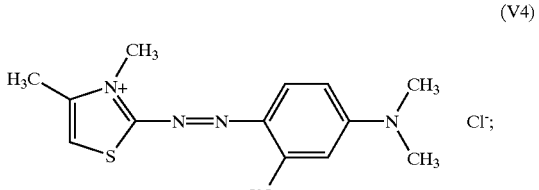

(V5) 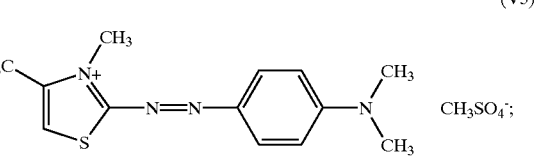

(V6) 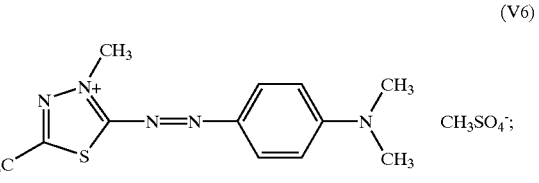

(V7) 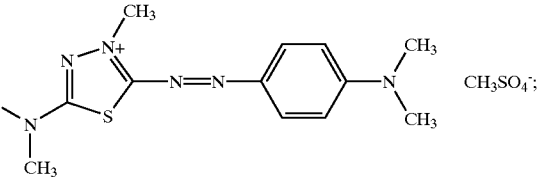

(V8) 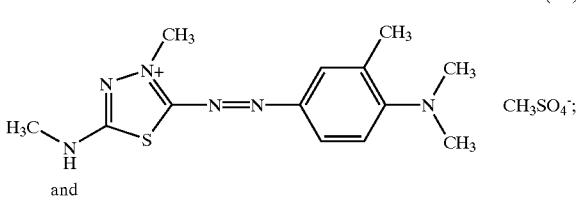

and

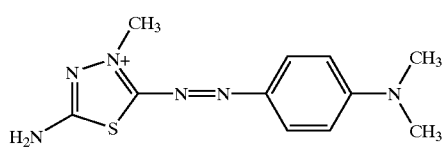 (V9)
Among the cationic direct dyes of formula (VI) which can be used in the dye compositions according to the invention, mention may be made more particularly of the compounds corresponding to the structures (VI1) to (VI18) below:
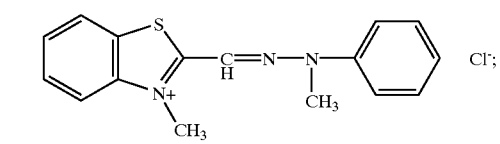 (VI1)
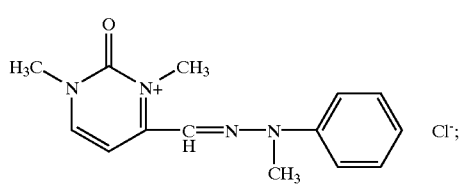 (VI2)
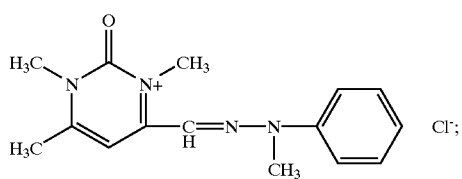 (VI3)
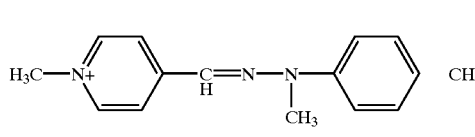 (VI4)
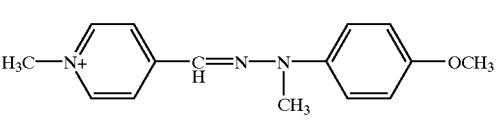 (VI5)
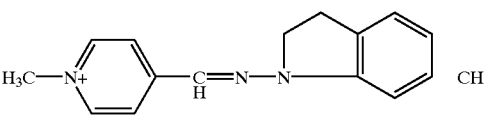 (VI6)
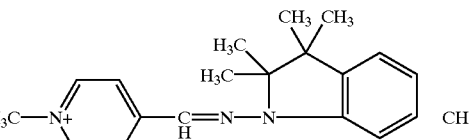 (VI7)
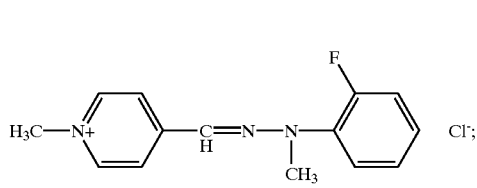 (VI8)
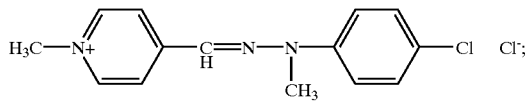 (VI9)
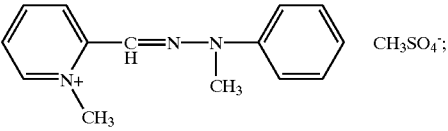 (VI10)
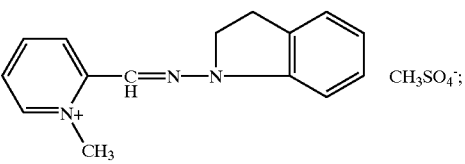 (VI11)
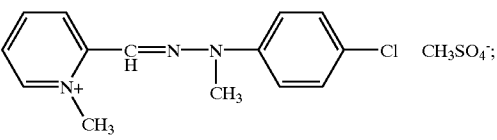 (VI12)
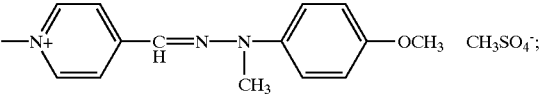 (VI13)
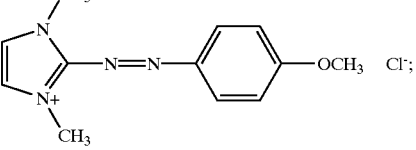 (VI14)
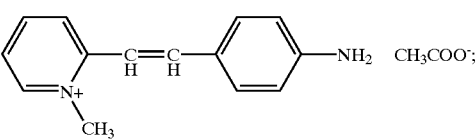 (VI15)
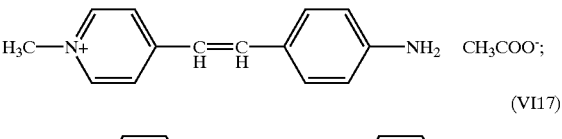 (VI16)
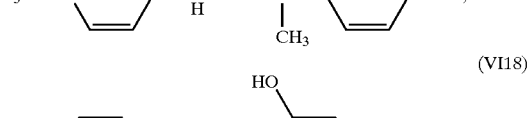 (VI17) and
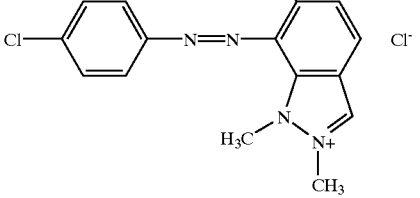 (VI18)

Among the specific compounds of the structures (VI1) to (VI18) described above, those most particularly preferred are the compounds corresponding to the structures (VI4), (VI5) and (VI13).

Among the cationic direct dyes of formula (VI') which can be used in the dye compositions according to the invention, mention may be made more particularly of the compounds corresponding to the structures (VI'1) to (VI'3) below:

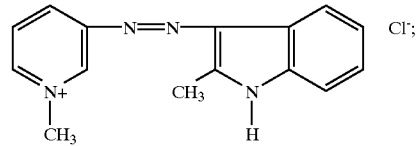
(VI'1)

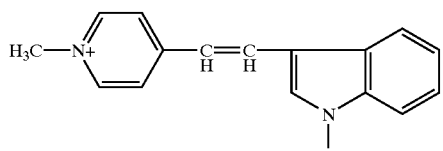
(VI'2) and

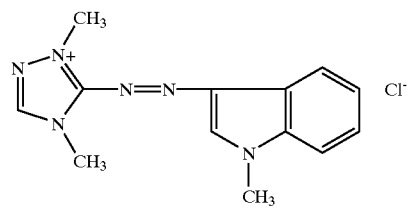
(VI'3)

Among the cationic direct dyes of formula (VII) which can be used in the dye compositions according to the invention, mention may be made more particularly of the compounds of the structures (VII1) to (VII77) below:

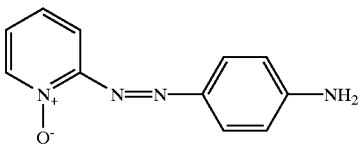
(VII1)

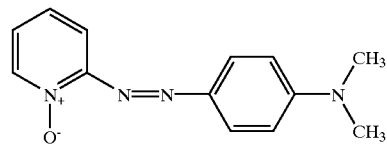
(VII2)

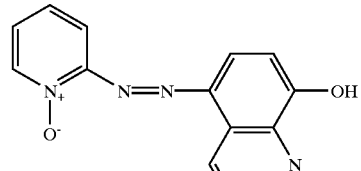
(VII3)

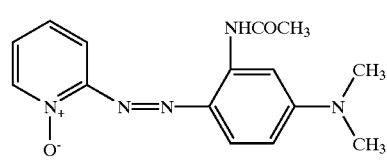
(VII4)

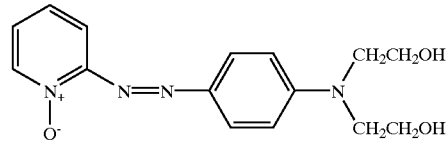
-continued
(VII5)

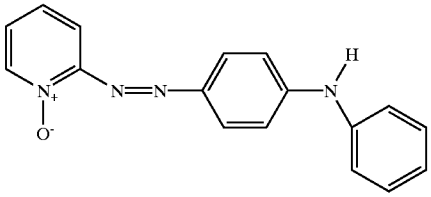
(VII6)

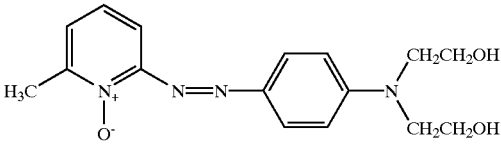
(VII7)

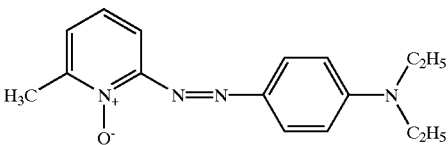
(VII8)

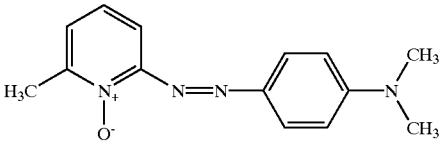
(VII9)

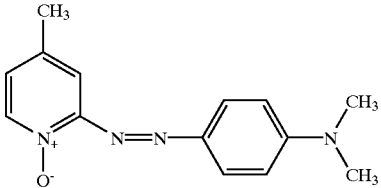
(VII10)

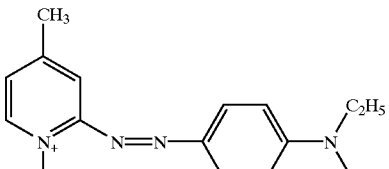
(VII11)

(VII12)

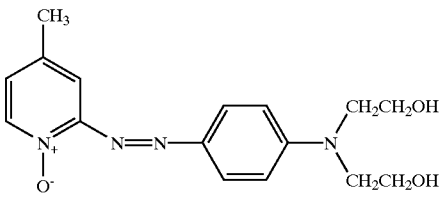

(VII13)
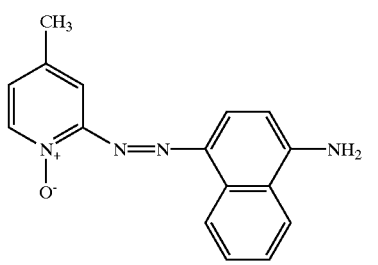
(VII14)
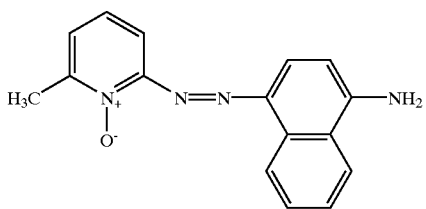
(VII15)
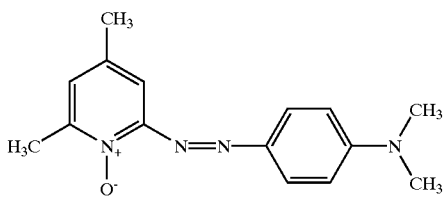
(VII16)
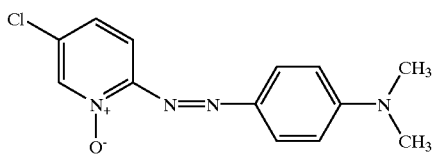
(VII17)
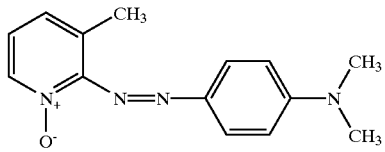
(VII18)
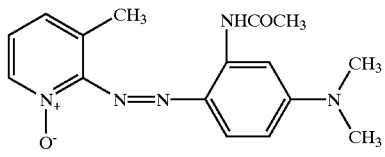
(VII19)
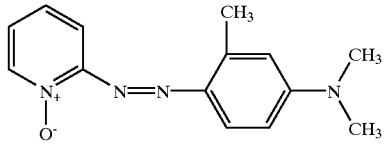
(VII20)
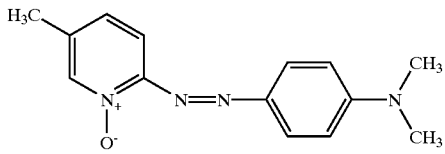
(VII21)
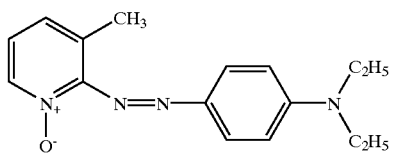
(VII22)
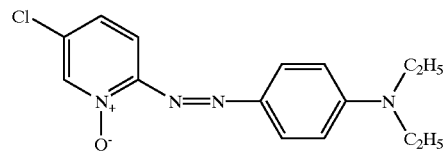
(VII23)
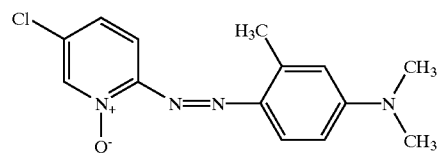
(VII24)
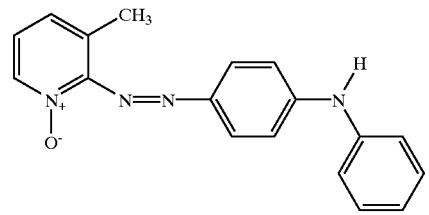
(VII25)
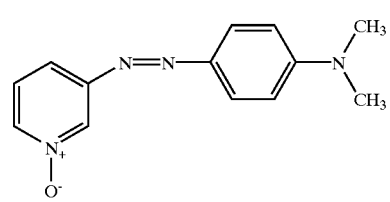
(VII26)
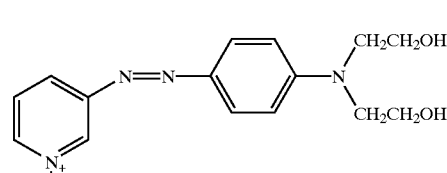
(VII27)
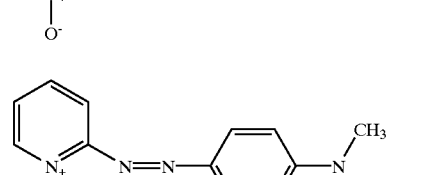
$CH_3SO_4^-$
(VII28)
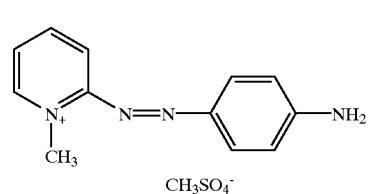
$CH_3SO_4^-$
(VII29)
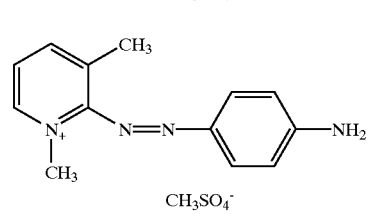
$CH_3SO_4^-$

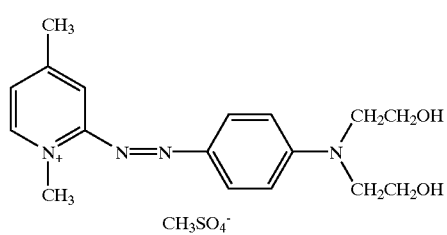
(VII30)
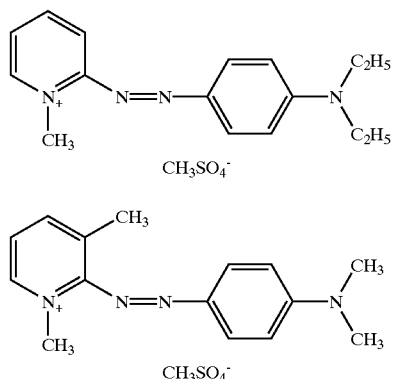
(VII31)
(VII32)
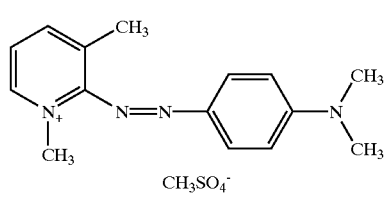
(VII33)
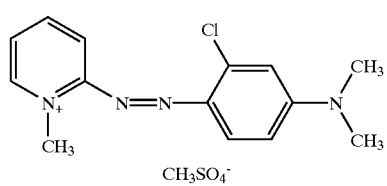
(VII34)
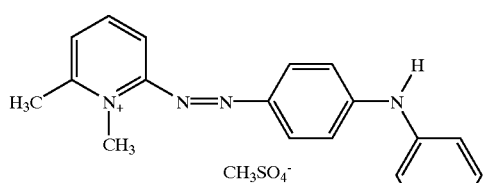
(VII35)
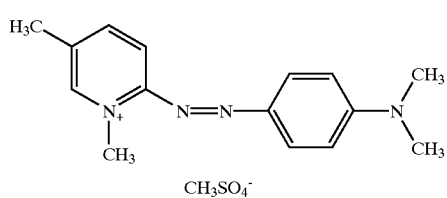
(VII36)
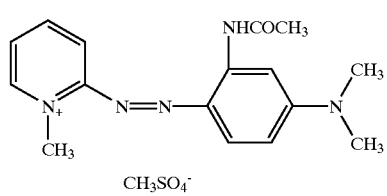
(VII37)
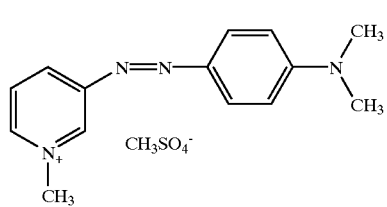
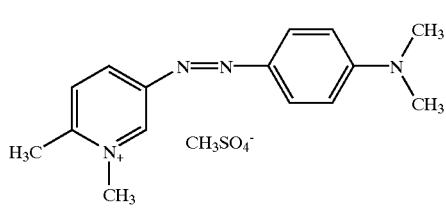
(VII38)
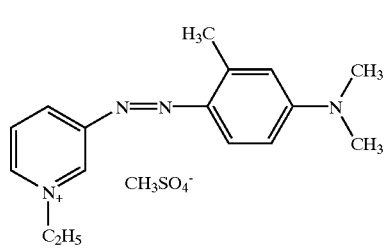
(VII39)
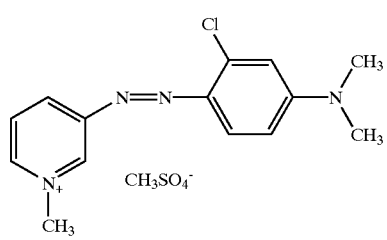
(VII40)
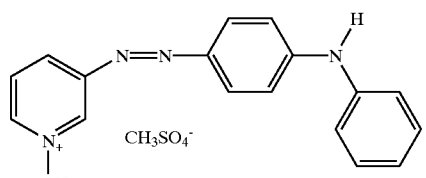
(VII41)
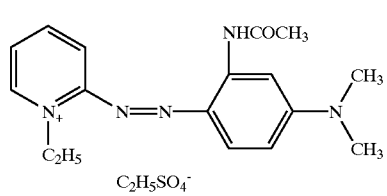
(VII42)
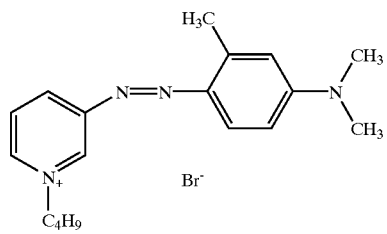
(VII43)
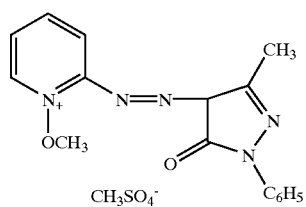
(VII44)

-continued (VII45)
(VII46)
(VII47)
(VII48)
(VII49)
(VII50)
(VII51)

-continued (VII52)
(VII53)
(VII54)
(VII55)
(VII56)
(VII57)
(VII58)
(VII59)

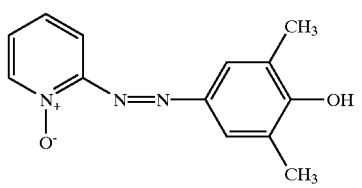
(VII60)
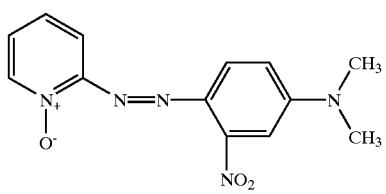
(VII61)
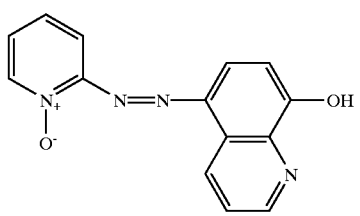
(VII62)
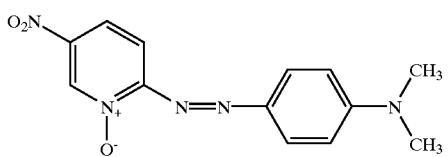
(VII63)
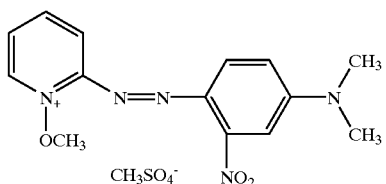
(VII64)
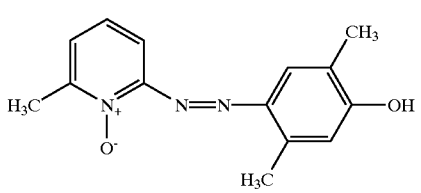
(VII65)
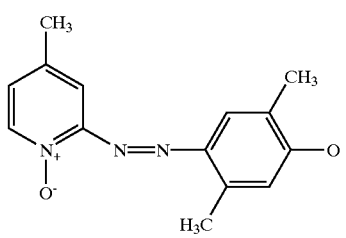
(VII66)
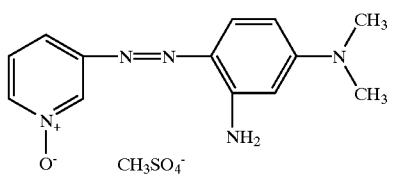
(VII67)
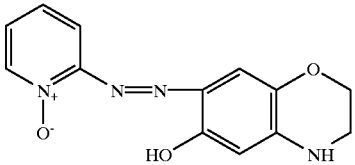
(VII68)
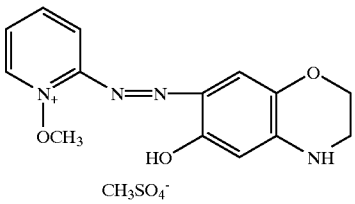
(VII69)
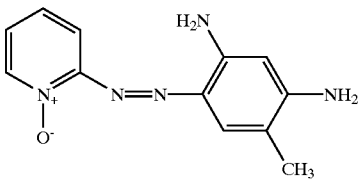
(VII70)
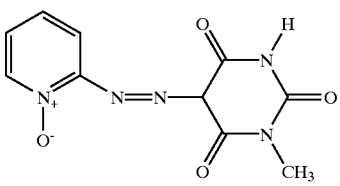
(VII71)
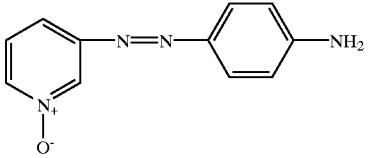
(VII72)
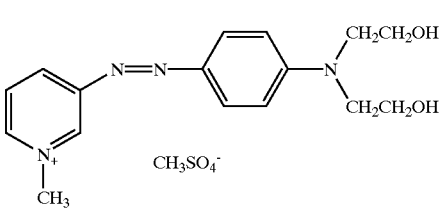
(VII73)
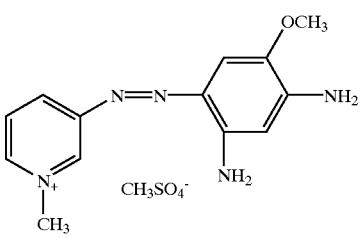
(VII74)
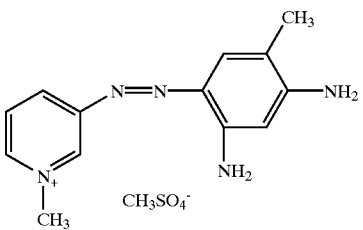
(VII75)

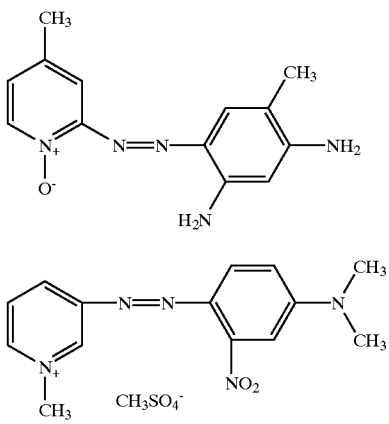

(VII76)

(VII77)

Another subject of the invention is a composition for the direct dyeing of keratin fibers, in particular human keratin fibers such as the hair, comprising, in a medium suitable for dyeing, a combination of cationic dyes of formulae (I) to (VII) as defined above, it being understand that the composition does not contain a self-oxidizing dye.

The cationic dye(s) of formulae (I) to (III) used according to the invention preferably represent from 0.001 to 10% by weight approximately relative to the total weight of the direct dye composition, and even more preferably from 0.005 to 5% by weight approximately relative to this weight.

The cationic dye(s) of formula (IV) to (VII) used according to the invention preferably represent from 0.001 to 10% by weight approximately relative to the total weight of the direct dye composition, and even more preferably from 0.005 to 5% by weight approximately relative to this weight.

The combination of cationic dyes of formulae (I) to (VII) according to the invention can also be used, as direct dyes, in well-known oxidation dyeing processes using oxidation dyes (oxidation dye precursors and optionally couplers), to vary the shades of the dyeing results obtained with the oxidation dyes or to enrich the dyeing results with glints.

In addition to the combination of cationic dyes of formulae (I) to (VII) according to the invention, the dye composition according to the invention can also contain, to broaden the range of shades and to obtain varied tints, other direct dyes conventionally used, in particular nitrobenzene dyes, anthraquinone dyes, naphthoquinone dyes, triarylmethane dyes, xanthine dyes and azo dyes that are non-cationic.

The medium suitable for dyeing (or support) generally comprises water or a I mixture of water and at least one organic solvent to dissolve the compounds which would not be sufficiently water-soluble. Organic solvents which may be mentioned, for example, are $C_1$–$C_4$ lower alkanols, such as ethanol and isopropanol, and aromatic alcohols such as benzyl alcohol, as well as similar products and mixtures thereof.

The solvents can be present in proportions preferably ranging from 1 to 40% by weight approximately relative to the total weight of the dye composition, and even more preferably from 5 to 30% by weight approximately.

The pH of the dye composition according to the invention ranges generally from 2 to 11 approximately, and preferably from 5 to 10 approximately. It can be adjusted to the desired value by means of acidifying or basifying agents usually used in the dyeing of keratin fibers.

Among the acidifying agents which may be mentioned, by way of example, are inorganic or organic acids such as hydrochloric acid, orthophosphoric acid, sulphuric acid, carboxylic acids such as acetic acid, tartaric acid, citric acid, lactic acid and sulphonic acids.

Among the basifying agents which may be mentioned, for example, are aqueous ammonia, alkaline carbonates, alkanolamines such as mono-, di- and triethanolamine as well as derivatives thereof, sodium hydroxide, potassium hydroxide and the compounds of formula (VIII) below:

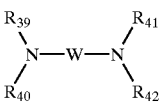

(VIII)

in which W is a propylene residue optionally substituted with a hydroxyl group or a $C_1$–$C_6$ alkyl radical; and $R_{39}$, $R_{40}$, $R_{41}$ and $R_{42}$, which may be identical or different, represent a hydrogen atom or a $C_1$–$C_6$ alkyl or $C_1$–$C_6$ hydroxyalkyl radical.

The direct dye composition according to the invention can also contain various adjuvants conventionally used in compositions for dyeing the hair, such as antioxidants, penetrating agents, sequestering agents, thickeners, fragrances, buffers, dispersants, anionic, nonionic, cationic or amphoteric surfactants, cationic, anionic, nonionic or amphoteric polymers, film-forming agents, ceramides, preserving agents, screening agents and opacifiers.

Needless to say, the person skilled in the art will select the optional additional compound(s) such that the advantageous properties associated with the dye composition according to the invention are not, or are not substantially, adversely affected by the addition(s).

The direct dye composition according to the invention can be in various forms, such as liquids, shampoos, creams or gels or in any other form which is suitable for dyeing keratin fibers, and in particular human hair. It can be obtained by mixing together, at the time of use, a composition, which may be pulverulent, containing a combination of cationic dyes of formulae (I) to (VII) defined above with an aqueous composition.

Another subject of the invention is a process for the direct dyeing of keratin fibers, and in particular of human keratin fibers such as the hair, using the dye composition as defined above.

According to a first variant of this direct dyeing process according to the invention, at least one dye composition as defined above is applied to the fibers, for a period which is sufficient to develop the desired dyeing results, after which the fibers are rinsed, optionally washed with shampoo and rinsed again, and dried.

The time required to develop the dyeing result on the keratin fibers ranges generally from 3 to 60 minutes and even more specifically from 5 to 40 minutes.

According to a second variant of this direct dyeing process according to the invention, at least one dye composition as defined above is applied to the fibers, for a period which is sufficient to develop the desired dyeing results, and dried without final rinsing.

Another subject of the invention is a multi-compartment dyeing device or "kit" or any other multi-compartment packaging system, a first compartment of which contains a composition containing the cationic dye of formulae (I) to (III) defined above, and a second compartment of which contains a composition containing the cationic dye of formulae (IV) to (VII) defined above. In one variant of the invention, the first compartment contains a pulverulent composition containing a combination of at least one cationic dye of formulae (I) to (III) and at least one cationic dye of formulae (IV) to (VII), and the second compartment contains an aqueous composition used as a vehicle for the dyeing operation. These devices can be equipped with a means for applying the desired mixture to the hair, such as the devices described in patent FR-2 586 913, the disclosure of which is incorporated by reference herein.

The prophetic examples which follow are intended to illustrate the invention without, however, limiting its scope.

EXAMPLES

Examples 1 to 4

The four direct dye compositions given in the table below are prepared:

(all contents expressed in grams)

|  | Example 1 | Example 2 | Example 3 | Example 4 |
|---|---|---|---|---|
| Arianor Madder Red (Warner Jenkinson) | 0.1 | | | |
| Arianor Steel Blue (Warner Jenkinson) | | 0.1 | 0.12 | |
| Arianor Straw Yellow (Warner Jenkinson) | | | | 0.12 |
| Cationic direct dye of formula (IV$_{31}$) | | 0.1 | | |
| Cationic direct dye of formula (VII$_{27}$) | | | 0.12 | |
| Cationic direct dye of formula (VI$_4$) | | | | 0.15 |
| Cationic direct dye of formula (IV$_1$) | 0.1 | | | |
| Hydroxyethylcellulose | 1.0 AM* | 1.0 AM* | 1.0 AM* | 1.0 AM* |
| Ethanol | 10 | 10 | 10 | 10 |
| 2-Amino-2-methyl-1-propanol qs | pH 9 | pH 9 | pH 9 | pH 9 |
| Demineralized water qs | 100 | 100 | 100 | 100 |

AM* denotes active material

The above compositions are each applied for 30 minutes to locks of natural grey hair containing 90% white hairs. the locks of hair are then rinsed, washed with a standard shampoo and then dried.

The locks are dyed in the following shades:

| Example | Shade obtained |
|---|---|
| 1 | intense red |
| 2 | intense blue-violet |
| 3 | intense violet |
| 4 | intense yellow |

What is claimed. is:

1. A dyeing composition for keratin fibers, comprising, in a medium suitable for dyeing, (i) at least one cationic dye of formulae (I) to (III) defined below, and (ii) at least one cationic dye of formulae (IV) to (VII) defined below, wherein said composition does not contain a self-oxidizing dye or an oxidizing agent:

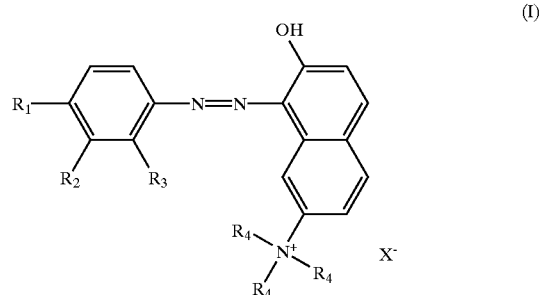
(I)

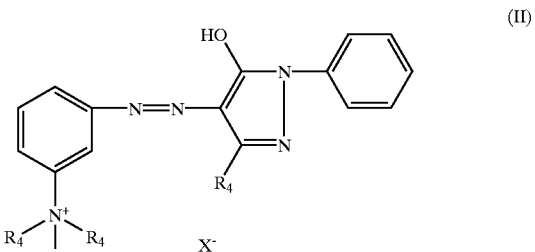
(II)

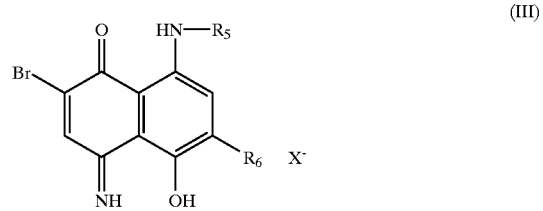
(III)

wherein:
$R_1$ is a hydrogen atom or an amino radical;
$R_2$ is a hydrogen atom or a nitro group;
$R_3$ is a hydrogen atom, a nitro group or a $C_1$–$C_4$ alkoxy radical;
$R_4$ is a $C_1$–$C_4$ alkyl radical;
$R_5$ is a hydrogen atom or a para-tri($C_1$–$C_4$) alkylammoniophenyl group;
$R_6$ is a bromine atom or an NH-para-tri-($C_1$–$C_4$) alkylammoniophenyl group; and
$X^-$ is an anion

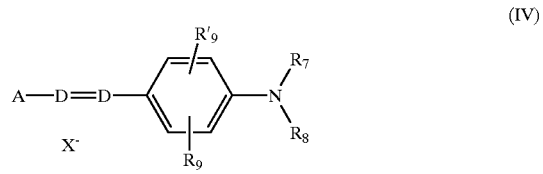
(IV)

wherein:
D is a nitrogen atom or a —CH group,
$R_7$ and $R_8$, which may be identical or different, are chosen from a hydrogen atom;
a 4'-aminophenyl radical; and a $C_1$–$C_4$ alkyl radical which can be substituted with a —CN, —OH or —NH$_2$ radical or which can form, with the nitrogen atom to which it is attached and with a carbon atom of the benzene ring of formula (IV), a heterocycle optionally comprising one or more oxygen atoms or additional nitrogen atoms, said heterocycle being optionally substituted with one or more identical or different $C_1$–$C_4$ alkyl radicals;
$R_9$ and $R'_9$, which may be identical or different, are chosen from a hydrogen atom; a halogen atom chosen from chlorine, bromine, iodine and fluorine; a cyano radical; a $C_1$–$C_4$ alkyl radical; a $C_1$–$C_4$ alkoxy radical; and an acetyloxy radical;

$X^-$ is an anion; and

A is a group chosen from structures A1 to A19 below:

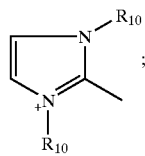 A₁

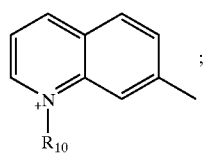 A₂

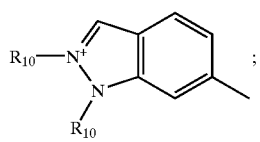 A₃

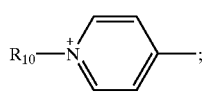 A₄

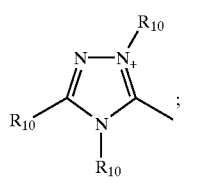 A₅

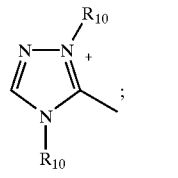 A₆

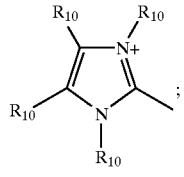 A₇

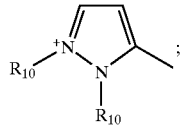 A₈

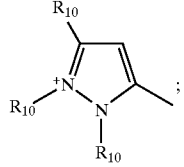 A₉

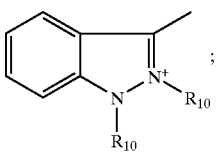 A₁₀

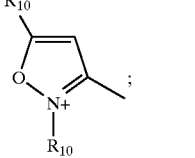 A₁₁

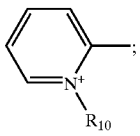 A₁₂

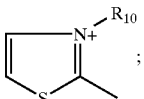 A₁₃

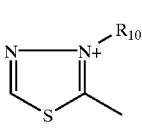 A₁₄

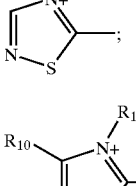 A₁₅

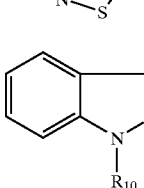 A₁₆

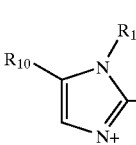 A₁₇

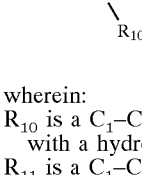 A₁₈ and

 A₁₉ wherein:

$R_{10}$ is a $C_1$–$C_4$ alkyl radical which can be substituted with a hydroxyl radical; and $R_{11}$ is a $C_1$–$C_4$ alkoxy radical;

with the overall provisos for formula (IV) that:

(i) when D is —CH, A is $A_4$ or $A_{13}$, and $R_9$ is other than an alkoxy radical, then at least one of $R_7$ and $R_8$ is not a hydrogen atom; and (ii) when D is a nitrogen atom, and A is $A_6$, then at least one of $R_7$ and $R_8$ is not a methyl radical;

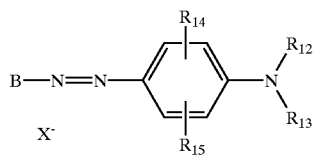

(V)

wherein:

$R_{12}$ is a hydrogen atom or a $C_1$–$C_4$ alkyl radical;

$R_{13}$ is chosen from a hydrogen atom; an alkyl radical which can be substituted with a —CN radical or with an amino group; and a 4'-aminophenyl radical; or wherein $R_{13}$ forms, together with $R_{12}$ and the nitrogen atom to which they are attached, a heterocycle optionally containing one or more oxygen atoms and/or additional nitrogen atoms, said heterocycle being optionally substituted with a $C_1$–$C_4$ alkyl radical;

$R_{14}$ and $R_{15}$, which may be identical or different, are chosen from a hydrogen atom, a halogen atom; a $C_1$–$C_4$ alkyl radical; a $C_1$–$C_4$ alkoxy radical; and a —CN radical;

$X^-$ is an anion; and

B is a group chosen from structures B1 to B6 below:

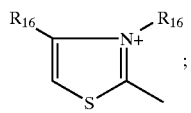

B1

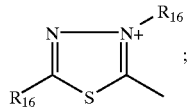

B2

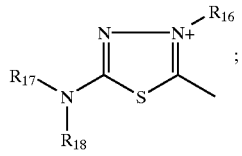

B3

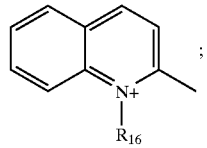

B4

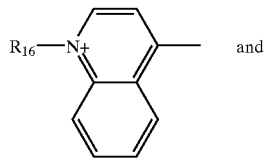

B5 and

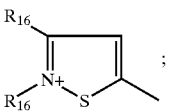

B6 wherein:

$R_{16}$ is a $C_1$–$C_4$ alkyl radical; and $R_{17}$ and $R_{18}$, which may be identical or different, are chosen from a hydrogen atom and a $C_1$–$C_4$ alkyl radical;

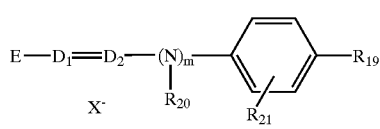

(VI)

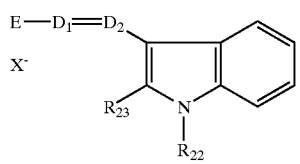

(VI¢)

wherein:

$R_{19}$ is chosen from a hydrogen atom; a $C_1$–$C_4$ alkoxy radical; a halogen atom; and an amino radical;

$R_{20}$ is a hydrogen atom or a $C_1$–$C_4$ alkyl radical; or wherein $R_{20}$ forms, with the nitrogen atom to which it is attached and with a carbon atom of the benzene ring of formula (VI), a heterocycle optionally comprising one or more oxygen atoms and optionally substituted with one or more identical or different $C_1$–$C_4$ alkyl groups;

$R_{21}$ is a hydrogen or a halogen atom;

$R_{22}$ and $R_{23}$, which may be identical or different, are chosen from a hydrogen atom and a $C_1$–$C_4$ alkyl radical;

$D_1$ and $D_2$, which may be identical or different, are chosen from a nitrogen atom and a —CH group;

m is equal to 0 or 1;

$X^-$ is an anion; and

E is a group chosen from structures E1 to E9 below:

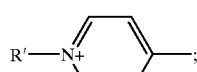

E1

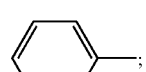

E2

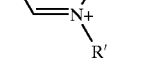

E3

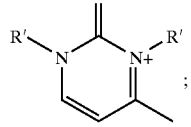

-continued

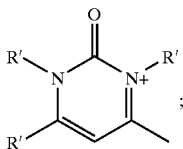
E4

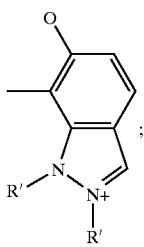
E5

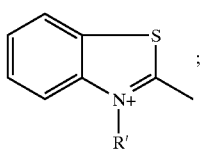
E6

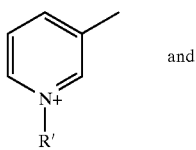
E7 and

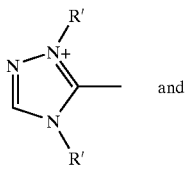
E8 and

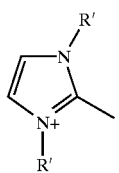
E9 wherein:
R' is a C$_1$–C$_4$ alkyl radical;

with the proviso that:

E can have the structure E9 only when m is equal to 0 and D$_1$ is a nitrogen atom;

with the overall proviso for formula (VI) that:

when R$_{19}$ is an unsubstituted amino group, then D$_1$ and D$_2$ are both —CH, and m is equal to 0;

$$G\text{—}N\text{=}N\text{—}J \quad (VII)$$

wherein:

G is a group chosen from structures G$_1$ to G$_3$ below:

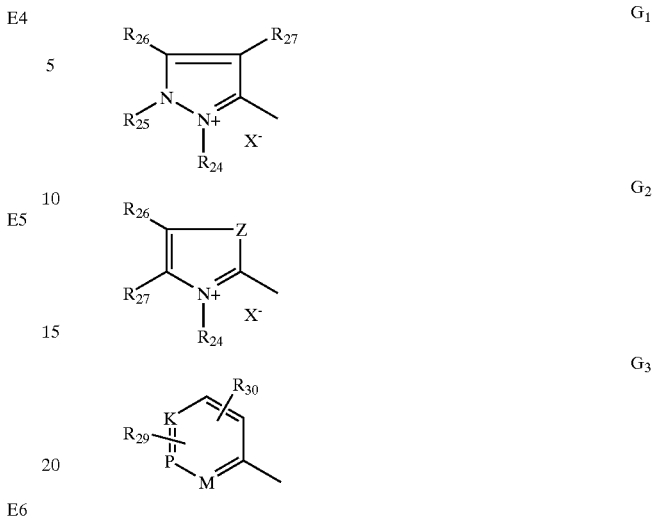

wherein
R$_{24}$ is chosen from a C$_1$–C$_4$ alkyl radical; a phenyl radical which can be substituted with a C$_1$–C$_4$ alkyl radical; and a halogen atom chosen from chlorine, bromine, iodine and fluorine:
R$_{25}$ is a C$_1$–C$_4$ alkyl radical or a phenyl radical:
R$_{26}$ is chosen from a hydrogen atom, a C$_1$–C$_4$ alkyl radical, and a phenyl radical; and R$_{27}$ is chosen from a C$_1$–C$_4$ alkyl radical and a phenyl radical;
or wherein R$_{26}$ and R$_{27}$ in formula G$_1$ together form a benzene ring substituted with one or more identical or different C$_1$–C$_4$ alkyl, C$_1$–C$_4$ alkoxy or N$_2$ radicals; or further wherein R$_{26}$ and R$_{27}$ in formula G$_2$ together form a benzene ring optionally substituted with one or more identical or different C$_1$–C$_4$ alkyl, C$_1$–C$_4$ alkoxy or N$_{02}$ radicals;
Z is chosen from an oxygen atom, a sulphur atom and a group —NR$_{25}$;
M, K and P, which may be identical or different, are chosen from —CH, —CR, and —NR$_{28}$(X$^-$)$_r$;
R is C$_1$–C$_4$;
r is equal to 0 or 1;
R$_{28}$ is chosen from an atom O$^-$, a C$_1$–C$_4$ alkoxy radical and a C$_1$–C$_4$ alkyl radical;
R$_{29}$ and R$_{30}$, which may be identical or different, are chosen from a hydrogen atom; a halogen atom chosen from chlorine, bromine, iodine and fluorine; a C$_1$–C$_4$ alkyl radical; a C$_1$–C$_4$ alkoxy radical; and an —NO$_2$ radical;
X$^-$ is an anion;
with the provisos that:
if R$_{28}$ is O$^-$, then r is zero;
if K, P or M is C$_1$–C$_4$—N-alkyl X$^-$, then at least one of R$_{29}$ or R$_{30}$ is other than a hydrogen atom;
if K is —NR$_{28}$(X$^-$)$_r$, then M is equal to P and is chosen from —CH and —CR;
if M is —NR$_{28}$(X$^-$)$_r$, then K is equal to P and is chosen from —CH and —CR;
if P is —NR$_{28}$(X$^-$)$_r$, then K is equal to M and is chosen from —CH and —CR;
if Z is a sulphur atom and R$_{27}$ is C$_1$–C$_4$ alkyl, then R$_{26}$ is other than a hydrogen atom; and
if Z is —NR$_{28}$ and R$_{25}$ is C$_1$–C$_4$ alkyl, then at least one of the radicals R$_{24}$, R$_{26}$ or R$_{27}$ of formula G$_2$ is other than a C$_1$–C$_4$ alkyl radical;

and

J is chosen from:

(a) a group of structure $J_1$ below:

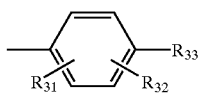   $J_1$ wherein $R_{31}$ is chosen from a hydrogen atom; a halogen atom chosen from chlorine, bromine, iodine and fluorine; a $C_1$–$C_4$ alkyl or $C_1$–$C_4$ alkoxy radical; and an —OH, —NO$_2$, —NHR$_{34}$, —NR$_{35}$R$_{36}$ and $C_1$–$C_4$—NHCO alkyl radical; or wherein $R_{31}$ forms, together with $R_{32}$, a 5- or 6-membered ring optionally comprising one or more identical or different hetero atoms chosen from nitrogen, oxygen and sulphur;

$R_{32}$ is chosen from a hydrogen atom; a halogen atom chosen from chlorine, bromine, iodine and fluorine; and a $C_1$–$C_4$ alkyl or $C_1$–$C_4$ alkoxy radical; or wherein $R_{32}$ forms, together with $R_{31}$, $R_{33}$ or $R_{34}$, a 5- or 6-membered ring optionally comprising one or more identical or different hetero atoms chosen from nitrogen, oxygen and sulphur;

$R_{33}$ is chosen from a hydrogen atom; an —OH radical; an —NHR$_{34}$ radical; and an —NR$_{35}$R$_{36}$ radical;

$R_{34}$ is chosen from a hydrogen atom; a $C_1$–$C_4$ alkyl radical; a $C_1$–$C_4$ monohydroxyalkyl radical; a $C_2$–$C_4$ polyhydroxyalkyl radical; and a phenyl radical; and $R_{35}$ and $R_{36}$, which may be identical or different, are chosen from a $C_1$–$C_4$ alkyl radical; a $C_1$–$C_4$ monohydroxyalkyl radical; and a $C_2$–$C_4$ polyhydroxyalkyl radical; and (b) a 5- or 6-membered nitrogenous heterocyclic group which can comprise one or more additional identical or different hetero atoms and/or one or more carbonyl groups and which can be substituted with one or more identical or different $C_1$–$C_4$ alkyl, amino or phenyl radicals.

2. A composition according to claim 1, wherein said keratin fibers are human keratin fibers.

3. A composition according to claim 2, wherein said human keratin fibers are hair.

4. A composition according to claim 1, wherein J is a 5- or 6-membered nitrogenous heterocyclic group of structure $J_2$ below:

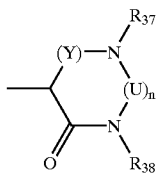   $J_2$ wherein:

$R_{37}$ and $R_{38}$, which may be identical or different, are chosen from a hydrogen atom, a $C_1$–$C_4$ alkyl radical and a phenyl radical;

Y is a —CO—radical or a radical;

n is equal to 0 or 1; and

U is a —CO— radical when n is equal to 1.

5. A composition according to claim 1, wherein the anion $X^-$ in formulae (I), (II), (III), (IV), (V) and (VI) is chosen from chloride, methylsulphate and acetate.

6. A composition according to claim 1, wherein the anion $X^-$ in the structures $G_1$, $G_2$ and $G_3$ is chosen from chloride, iodide, methyl sulphate, ethyl sulphate, acetate and perchlorate.

7. A composition according to claim 1, wherein $R_{14}$ and $R_{15}$ in formula (V) are chosen from a hydrogen atom; a halogen atom chosen from bromine, chlorine, iodine and fluorine; a $C_1$–$C_4$ alkyl or $C_1$–$C_4$ alkoxy radical; and a —CN radical.

8. A composition according to claim 1, wherein Rlg in formula (VI) is chosen from a hydrogen atom; a $C_1$–$C_4$ alkoxy radical; a halogen atom chosen from bromine, chlorine, iodine and fluorine; and an amino radical.

9. A composition according to claim 1, wherein $R_{21}$ in formula (VI) is chosen from hydrogen, bromine, chlorine, iodine and fluorine atoms.

10. A composition according to claim 1, wherein said at least one cationic dye of formula (I) is chosen from Basic Brown 17, Basic Brown 16, Basic Red 76 and Basic Red 118.

11. A composition according to claim 1, wherein said at least one cationic dye of formula (II) is Basic Yellow 57.

12. A composition according to claim 1, wherein said at least one cationic dye of formula (III) is Basic Blue 99.

13. A composition according to claim 1, wherein said at least one cationic dye of formula (IV) is chosen from the compounds of formulae (IV1) to (IV54) below:.

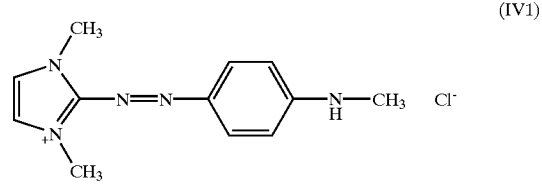   (IV1)

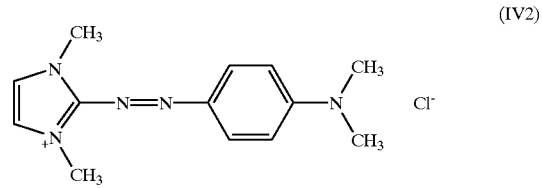   (IV2)

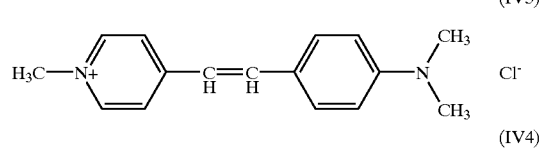   (IV3)

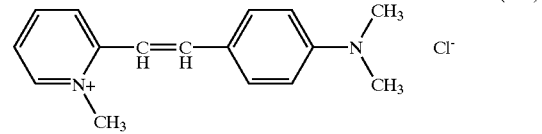   (IV4)

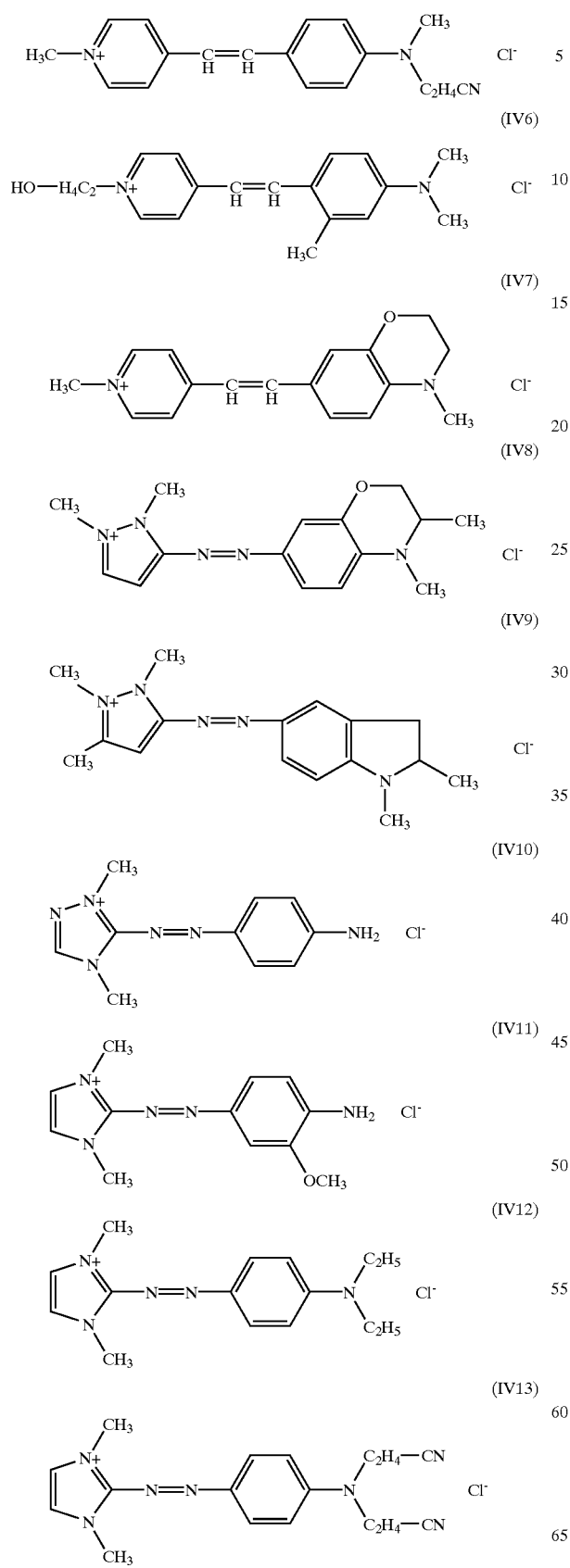

(IV22)
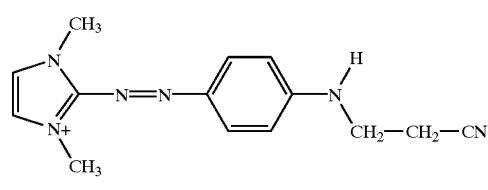
(IV23)
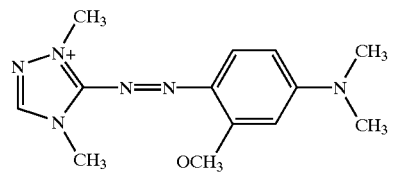
(IV24)
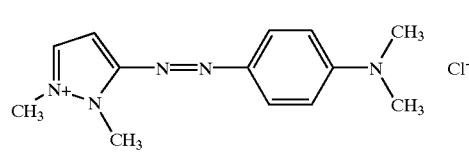
(IV25)
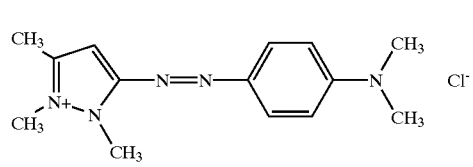
(IV26)
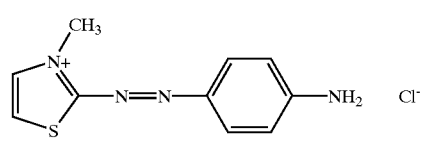
(IV27)
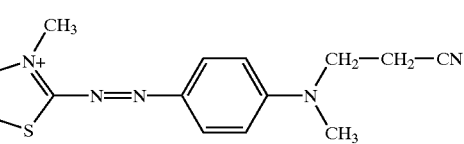
(IV28)
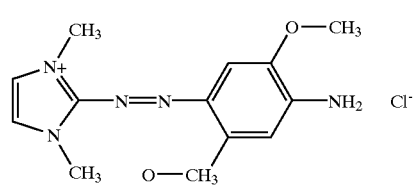
(IV29)
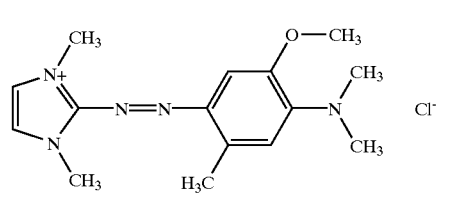
(IV30)
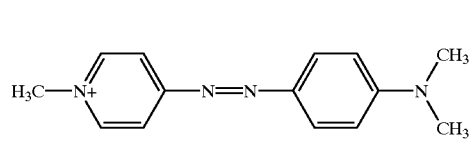
(IV31)
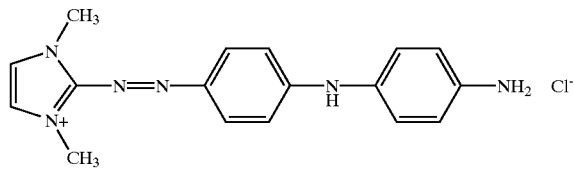
(IV32)
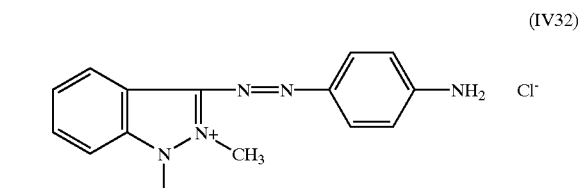
(IV33)
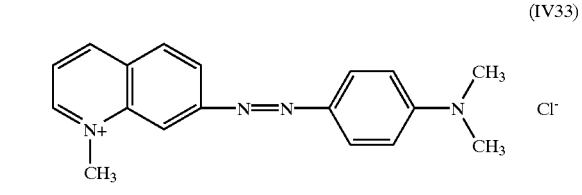
(IV34)
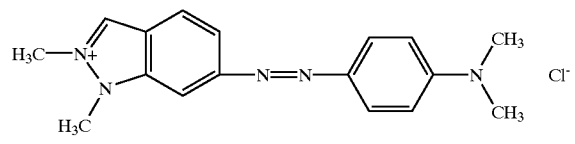
(IV35)
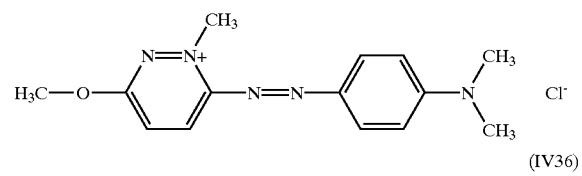
(IV36)
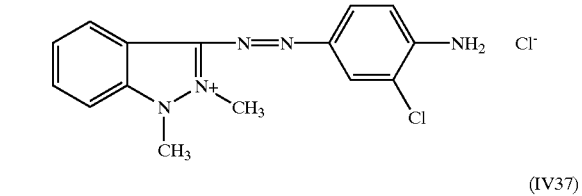
(IV37)
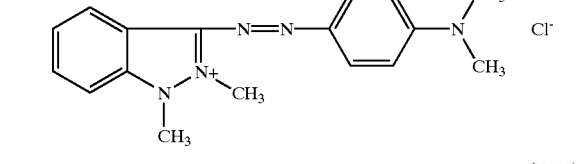
(IV38)
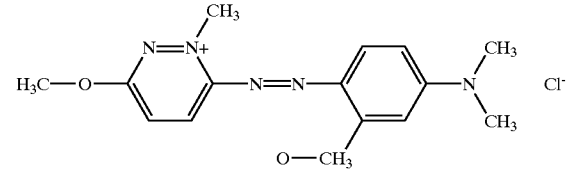

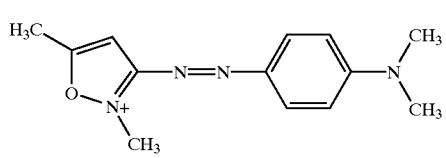 (IV39)
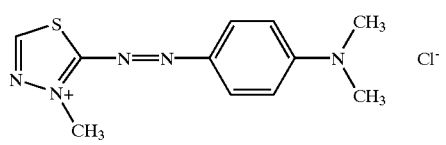 (IV40)
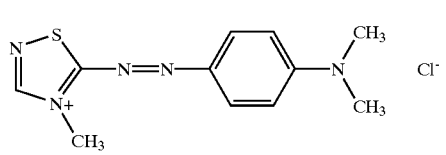 (IV41)
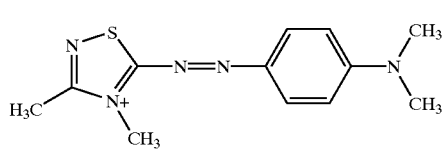 (IV42)
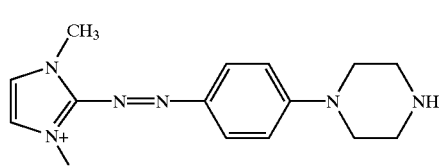 (IV43)
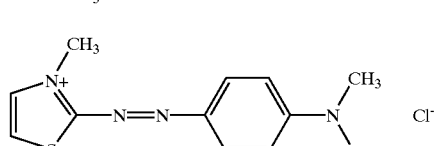 (IV44)
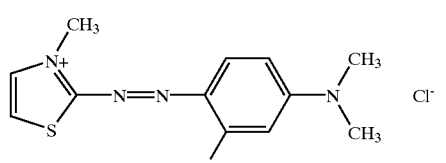 (IV45)
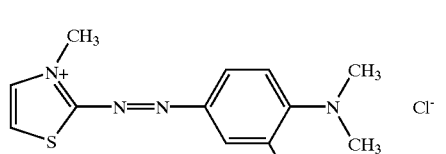 (IV46)
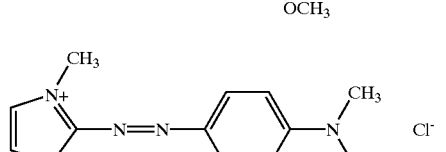 (IV47)
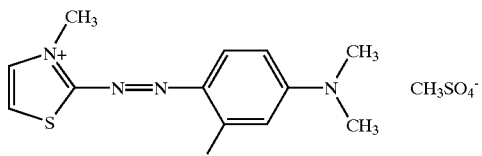 (IV48)
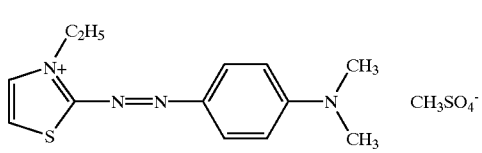 (IV49)
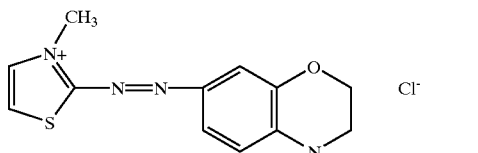 (IV50)
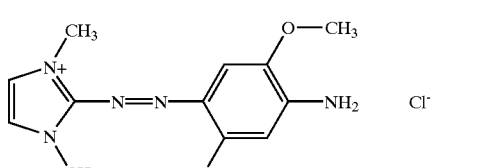 (IV51)
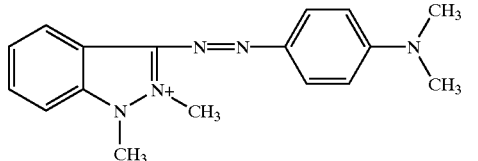 (IV52)
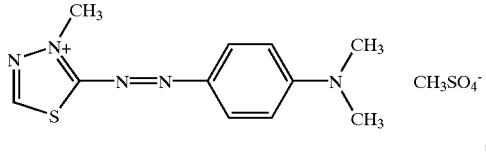 (IV53)
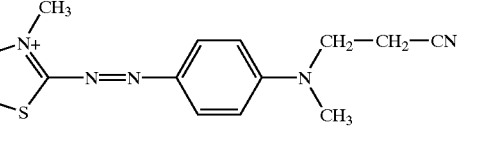 (IV54)
14. A composition according to claim 13, wherein said at least one cationic dye of formula (IV) is chosen from the compounds of formulae (IV1), (IV2), (IV14) and (IV31).
15. A composition according to claim 1, wherein said at least one cationic dye of formula (V) is chosen from the compounds of formulae (V1) to (V9) below:
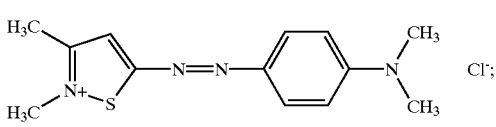 (V1)

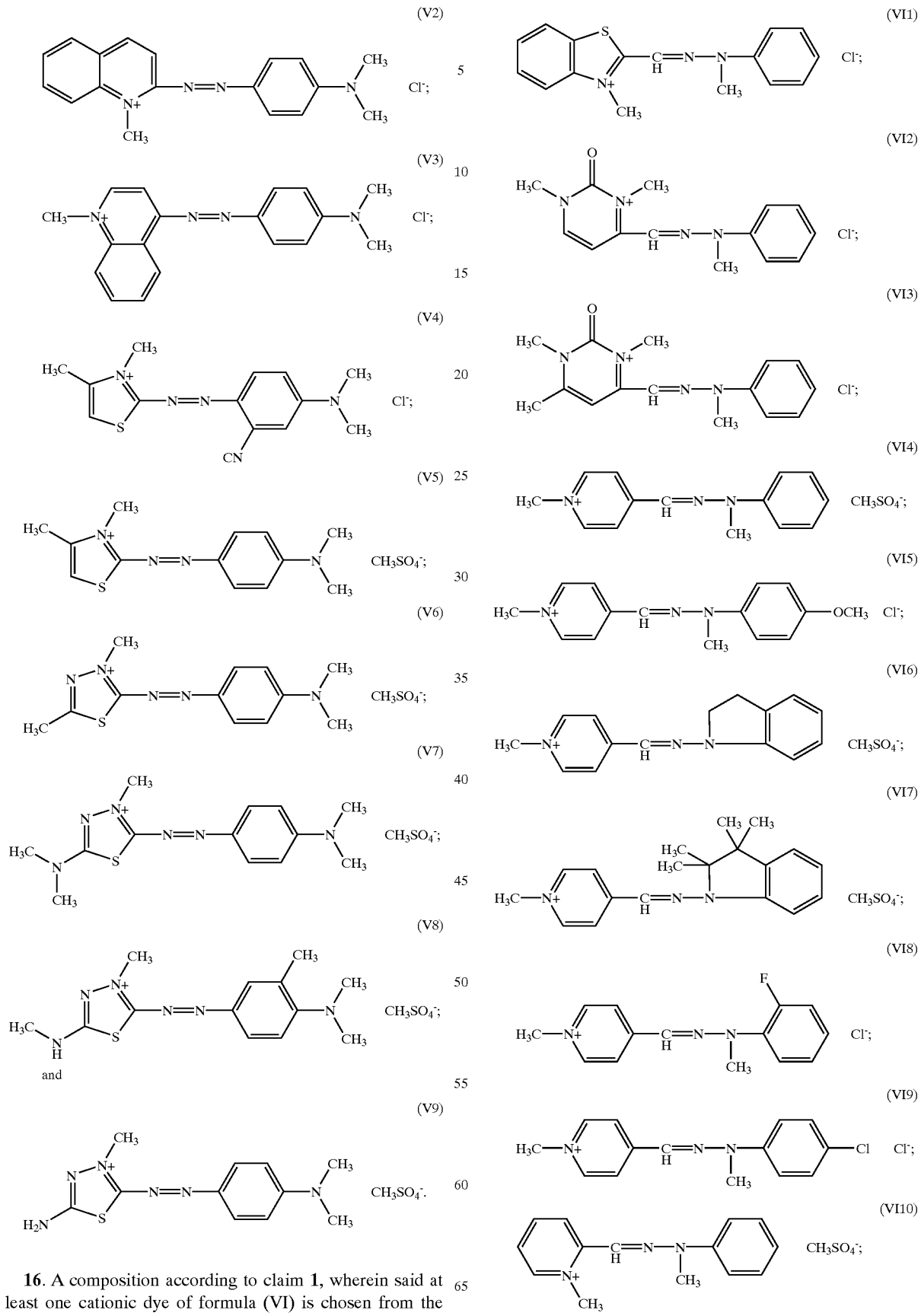
16. A composition according to claim 1, wherein said at least one cationic dye of formula (VI) is chosen from the compounds of formulae (VI1) to (VI18) below:

-continued

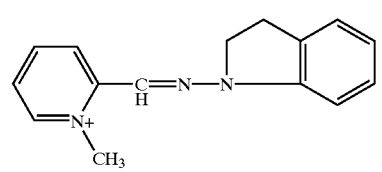 (VI11) CH₃SO₄⁻;

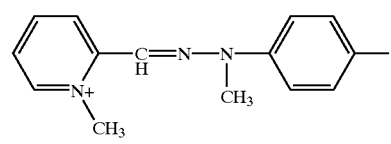 (VI12) CH₃SO₄⁻;

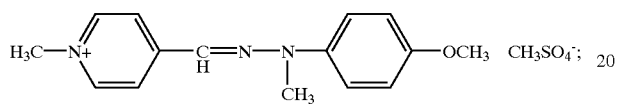 (VI13) CH₃SO₄⁻;

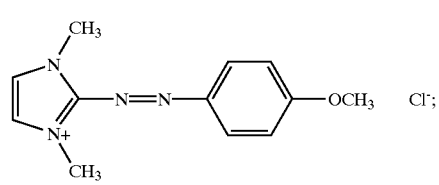 (VI14) Cl⁻;

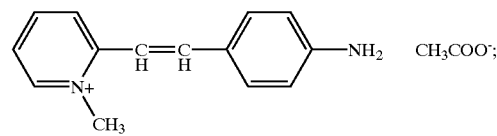 (VI15) CH₃COO⁻;

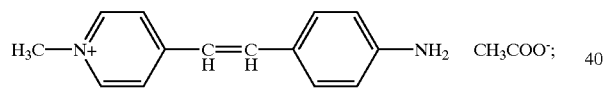 (VI16) CH₃COO⁻;

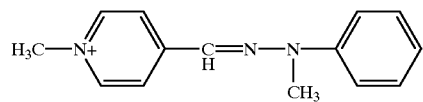 (VI17) Cl⁻;

and

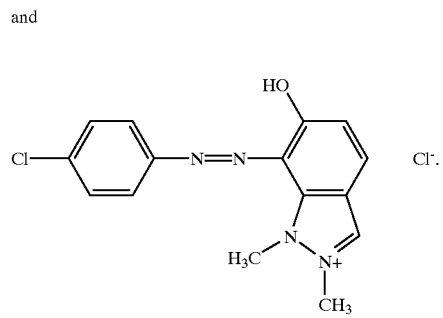 (VI18) Cl⁻.

17. A composition according to claim 16, wherein said at least one cationic dye of formula (VI) is chosen from the compounds of formula (VI4), (VI5) and (VI13).

18. A composition according to claim 1, wherein said at least one cationic dye of formula (VI') is chosen from the compounds of formulae (VI'1) to (VI'3) below:

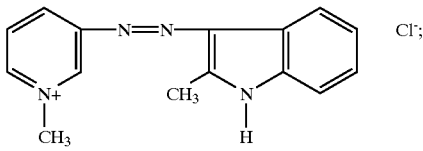 (VI'1) Cl⁻;

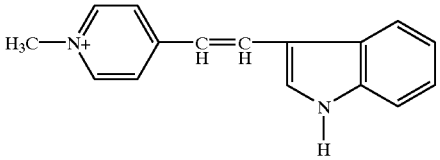 (VI'2) Cl⁻;

and

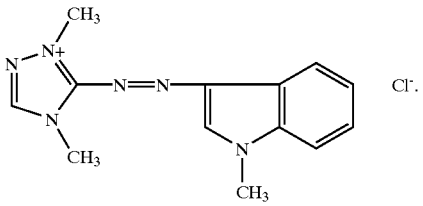 (VI'3) Cl⁻.

19. A composition according to claim 1, wherein said at least one cationic dye of formula (VII) is chosen from the compounds of formulae (VII1) to (VII77) below:

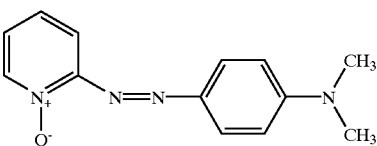 (VII1)

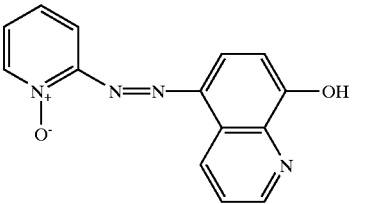 (VII2)

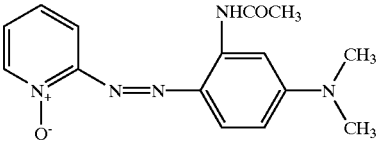 (VII3)

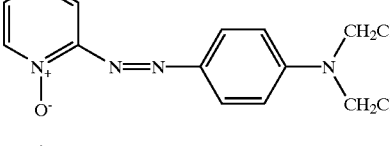 (VII4)

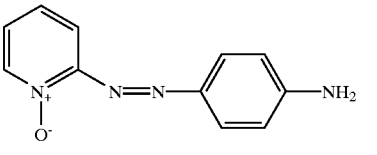 (VII5)

-continued (VII6)
(VII7)
(VII8)
(VII9)
(VII10)
(VII11)
(VII12)
(VII13)
(VII14)
(VII15)
(VII16)
(VII17)
(VII18)
(VII19)
(VII20)
(VII21)
(VII22)

(VII23)
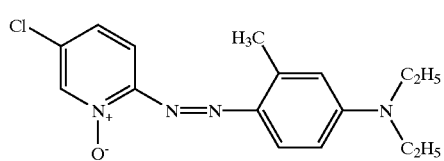
(VII24)
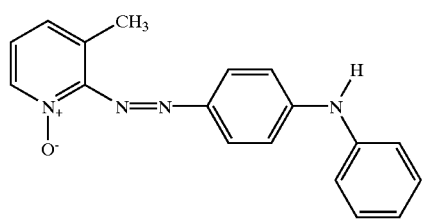
(VII25)
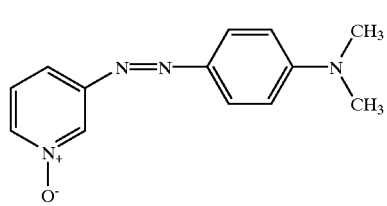
(VII26)
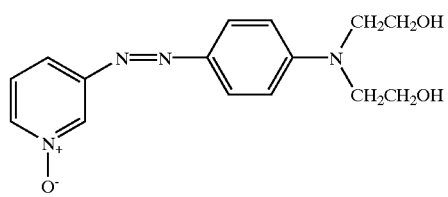
(VII27)
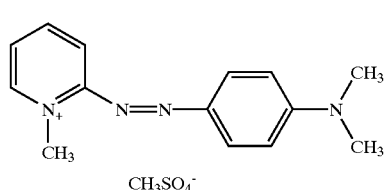
CH$_3$SO$_4^-$
(VII28)
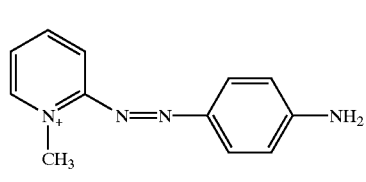
CH$_3$SO$_4^-$
(VII29)
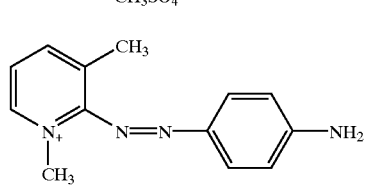
CH$_3$SO$_4^-$
(VII30)
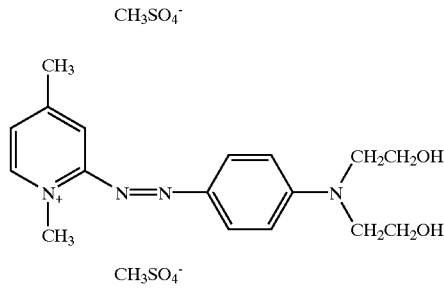
CH$_3$SO$_4^-$
(VII31)
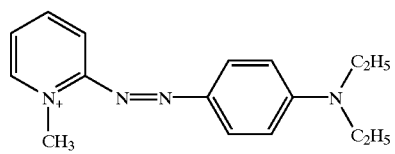
CH$_3$SO$_4^-$
(VII32)
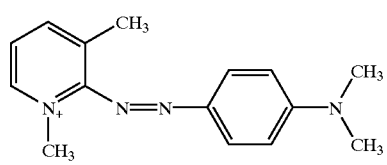
CH$_3$SO$_4^-$
(VII33)
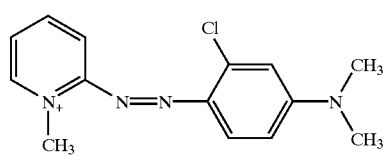
CH$_3$SO$_4^-$
(VII34)
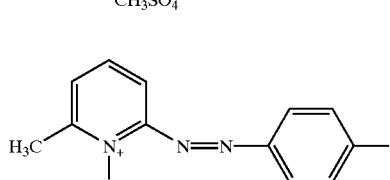
CH$_3$SO$_4^-$
(VII35)
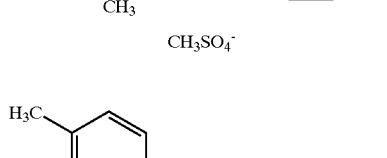
CH$_3$SO$_4^-$
(VII36)
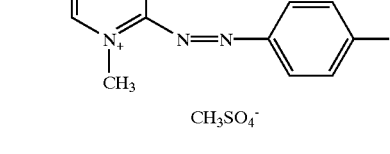
CH$_3$SO$_4^-$
(VII37)
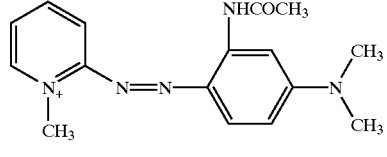
CH$_3$SO$_4^-$
(VII38)
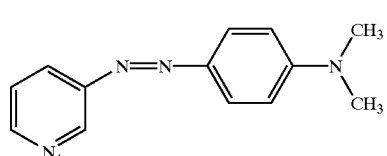
CH$_3$SO$_4^-$
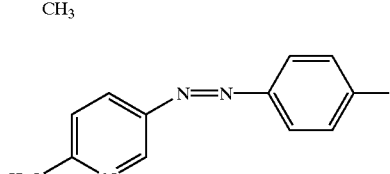

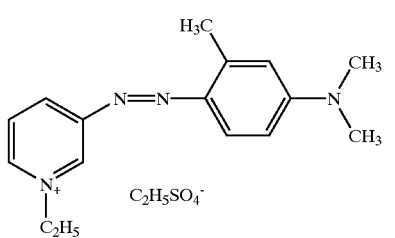 (VII39)
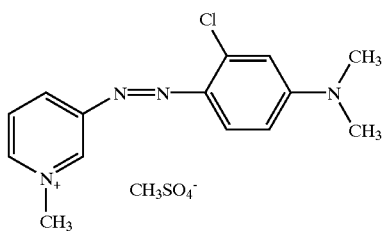 (VII40)
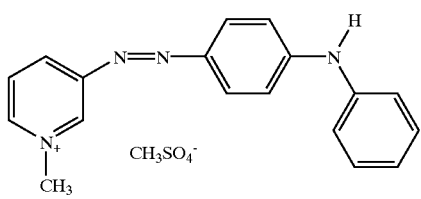 (VII41)
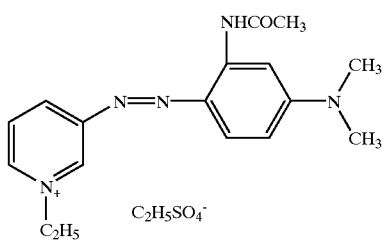 (VII42)
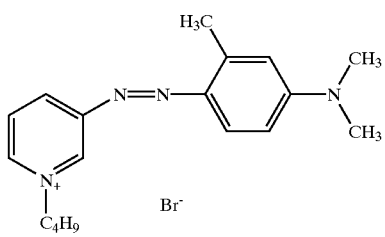 (VII43)
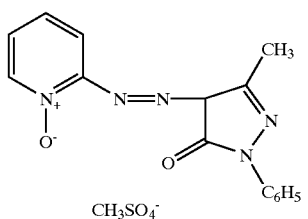 (VII44)
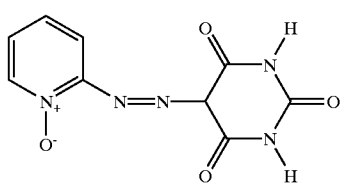 (VII45)
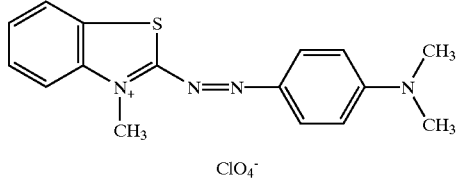 (VII46)
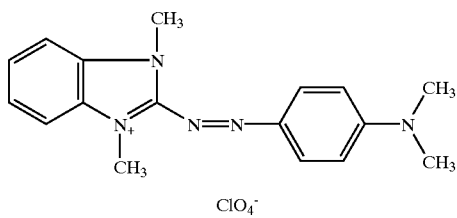 (VII47)
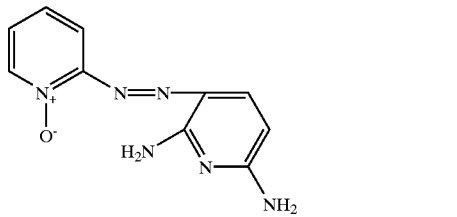 (VII48)
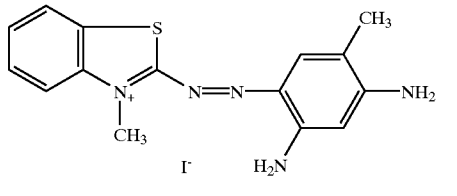 (VII49)
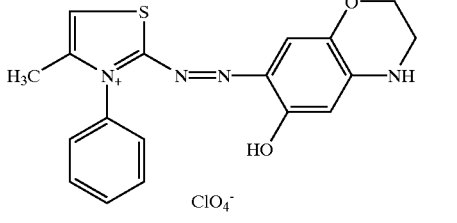 (VII50)
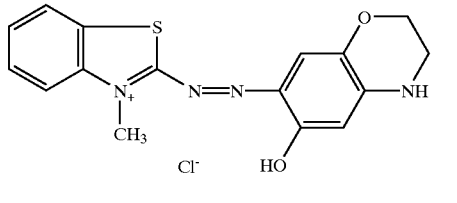 (VII51)
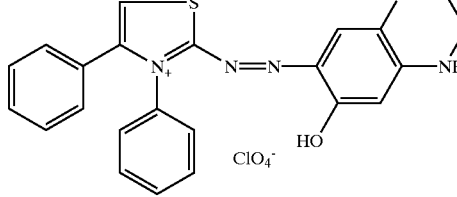 (VII52)

-continued
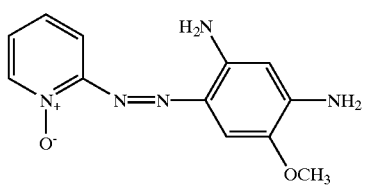 (VII53)
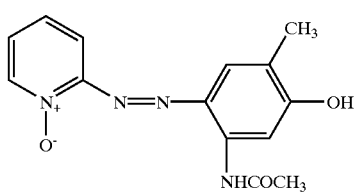 (VII54)
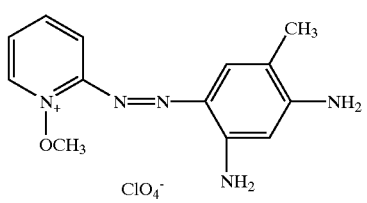 (VII55)
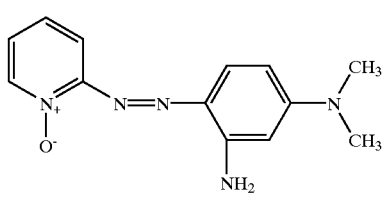 (VII56)
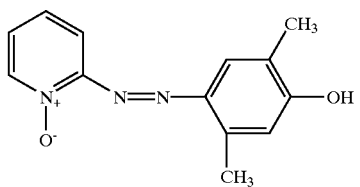 (VII57)
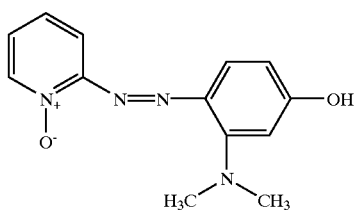 (VII58)
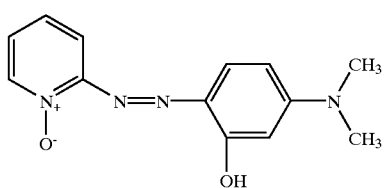 (VII59)
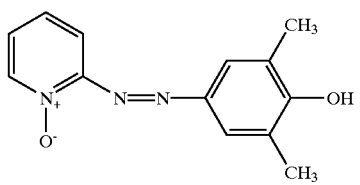 (VII60)
-continued
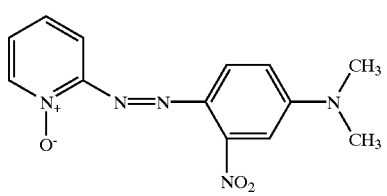 (VII61)
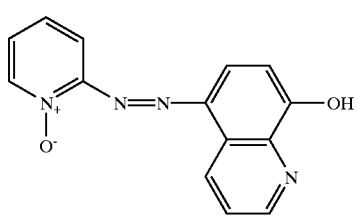 (VII62)
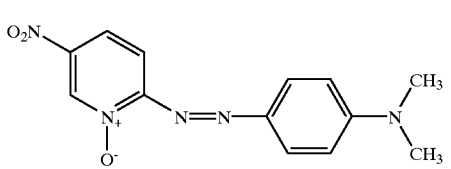 (VII63)
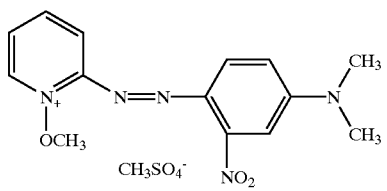 (VII64)
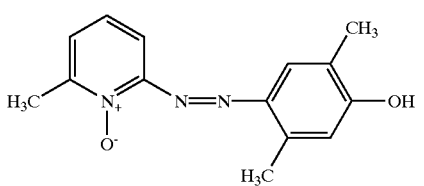 (VII65)
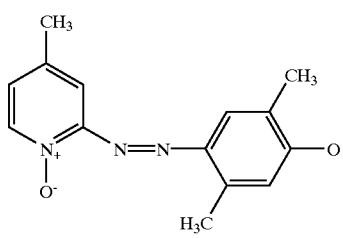 (VII66)
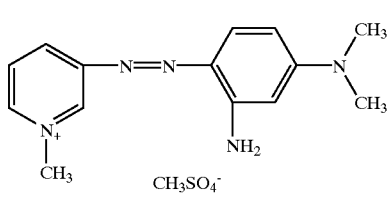 (VII67)
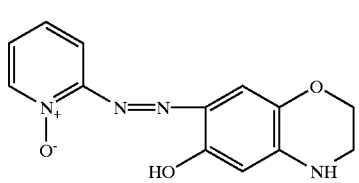 (VII68)

(VII69) 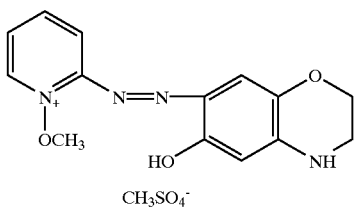

(VII70) 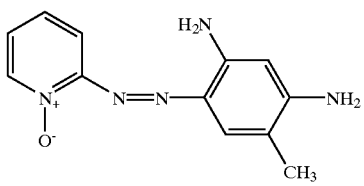

(VII71) 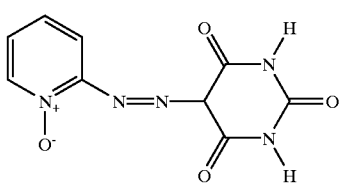

(VII72) 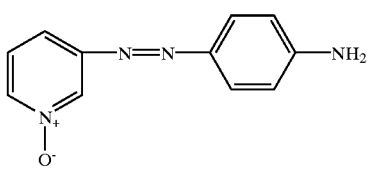

(VII73) 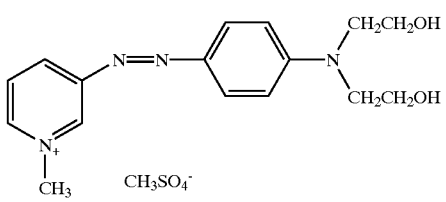

(VII74) 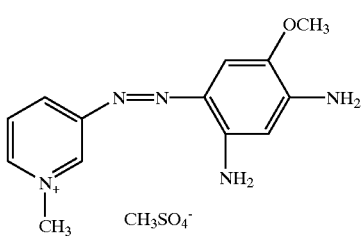

(VII75) 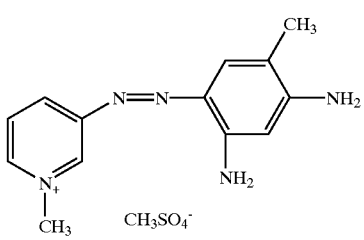

(VII76) 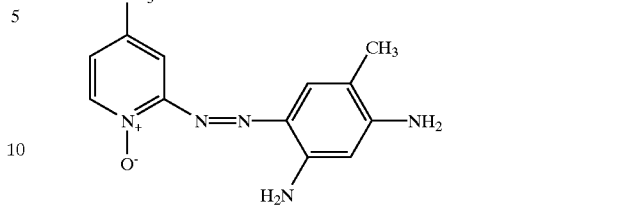

(VII77) 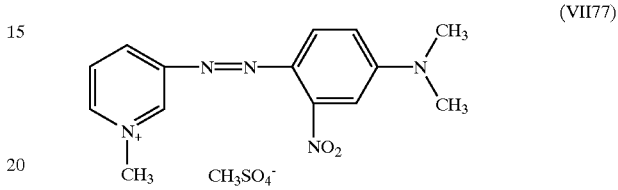

20. A composition according to claim 1, wherein said at least one cationic dye of formulae (I), (II) or (III) is present in an amount ranging from 0.001 to 10% by weight relative to the total weight of the composition.

21. A composition according to claim 20, wherein said at least one cationic dye of formulae (I), (II) or (III) is present in an amount ranging from 0.005 to 5% by weight relative to the total weight of the composition.

22. A composition according to claim 1, wherein said at least one cationic dye of formulae (IV), (V), (VI), (VI') or (VII) is present in an amount ranging from 0.001 to 10% by weight relative to the total weight of the composition.

23. A composition according to claim 22, wherein said at least one cationic dye of formulae (IV), (V), (VI), (VI') or (VII) is present in an amount ranging from 0.005 to 5% by weight relative to the total weight of the composition.

24. A composition according to claim 1, wherein said medium suitable for dyeing comprises water or a mixture of water and at least one organic solvent.

25. A composition according to claim 1, wherein said composition has a pH ranging from 2 to 11.

26. A composition according to claim 25, wherein said composition has a pH ranging from 5 to 10.

27. A composition according to claim 1, wherein said composition additionally comprises adjuvants chosen from antioxidants, penetrating agents, sequestering agents, thickeners, fragrances, buffers, dispersants, surfactants, polymers, film-forming agents, ceramides, preserving agents, screening agents and opacifiers.

28. A process for dyeing keratin fibres by direct dyeing, comprising applying a dye composition to keratin fibres, said dye composition comprising, in a medium suitable for dyeing, (i) at least one cationic dye of formulae (I) to (III) defined below, and (ii) at least one cationic dye of formulae (IV) to (VII) defined below, wherein said composition does not contain a self-oxidizing dye or an oxidizing agent, said composition being allowed to act on said fibers for a period which is sufficient to develop the desired dyeing results:

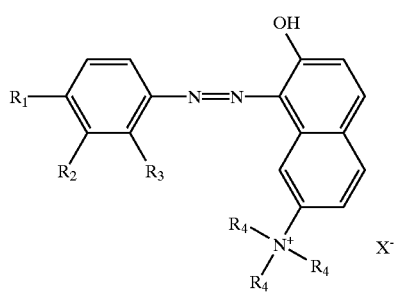
(I)

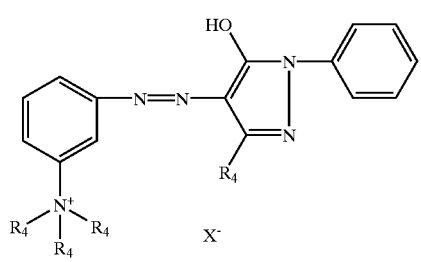
(II)

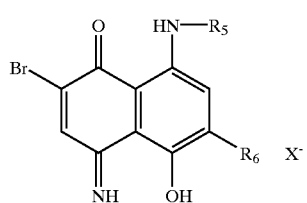
(III)

wherein:
  $R_1$ is a hydrogen atom or an amino radical;
  $R_2$ is a hydrogen atom or a nitro group;
  $R_3$ is a hydrogen atom, a nitro group or a $C_1$–$C_4$ alkoxy radical;
  $R_4$ is a $C_1$–$C_4$ alkyl radical;
  $R_5$ is a hydrogen atom or a para-tri($C_1$–$C_4$)alkylammoniophenyl group;
  $R_6$ is a bromine atom or an NH-para-tri-($C_1$–$C_4$)alkylammoniophenyl group; and
  $X^-$ is an anion

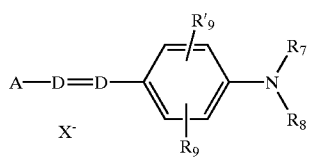
(IV)

wherein:
  D is a nitrogen atom or a —CH group,
  $R_7$ and $R_8$, which may be identical or different, are chosen from a hydrogen atom;
  a 4'-aminophenyl radical; and a $C_1$–$C_4$ alkyl radical which can be substituted with a —CN, —OH or —NH$_2$ radical or which can form, with the nitrogen atom to which it is attached and with a carbon atom of the benzene ring of formula (IV), a heterocycle optionally comprising one or more oxygen atoms or additional nitrogen atoms, said heterocycle being optionally substituted with one or more identical or different $C_1$–$C_4$ alkyl radicals;

$R_9$ and $R'_9$, which may be identical or different, are chosen from a hydrogen atom; a halogen atom chosen from chlorine, bromine, iodine and fluorine; a cyano radical; a $C_1$–$C_4$ alkyl radical; a $C_1$–$C_4$ alkoxy radical; and an acetyloxy radical;

$X^-$ is an anion; and

A is a group chosen from structures A1 to A19 below:

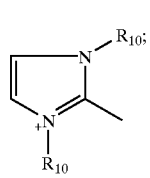
A1

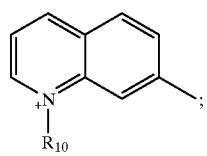
A2

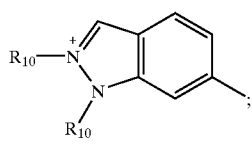
A3

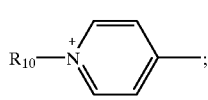
A4

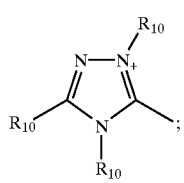
A5

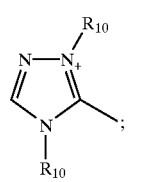
A6

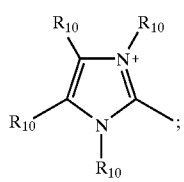
A7

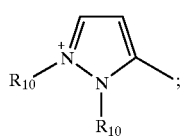
A8 wherein:
R₁₀ is a C₁–C₄ alkyl radical which can be substituted with a hydroxyl radical; and
R₁₁ is a C₁–C₄ alkoxy radical;

with the overall provisos for formula (IV) that:
(i) when D is —CH, A is A₄ or A₁₃, and R₉ is other than an alkoxy radical, then at least one of R₇ and R₈ is not a hydrogen atom; and
(ii) when D is a nitrogen atom, and A is A₆, then at least one of R₇ and R₈ is not a methyl radical;

(V)

wherein:
R₁₂ is a hydrogen atom or a C₁–C₄ alkyl radical;
R₁₃ is chosen from a hydrogen atom; an alkyl radical which can be substituted with a —CN radical or with an amino group; and a 4'-aminophenyl radical; or
wherein R₁₃ forms, together with R₁₂ and the nitrogen atom to which they are attached, a heterocycle optionally containing one or more oxygen atoms and/or additional nitrogen atoms, said heterocycle being optionally substituted with a C₁–C₄ alkyl radical;
R₁₄ and R₁₅, which may be identical or different, are chosen from a hydrogen atom, a halogen atom; a C₁–C₄ alkyl radical; a C₁–C₄ alkoxy radical; and a —CN radical;
X is an anion; and
B is a group chosen from structures B1 to B6 below:

-continued

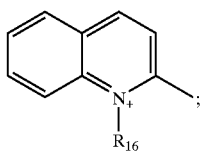
B4

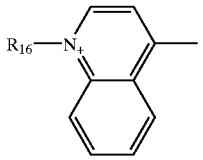
B5 and

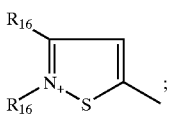
B6 wherein:
R$_{16}$ is a C$_1$–C$_4$ alkyl radical; and
R$_{17}$ and R$_8$, which may be identical or different, are chosen from a hydrogen atom and a C$_1$–C$_4$ alkyl radical;

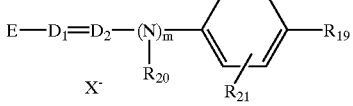
(VI)

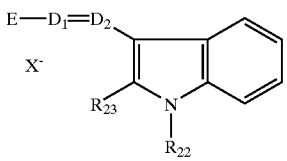
(VI')

wherein:
R$_{19}$ is chosen from a hydrogen atom; a C$_1$–C$_4$ alkoxy radical; a halogen atom; and an amino radical;
R$_{20}$ is a hydrogen atom or a C$_1$–C$_4$ alkyl radical; or wherein R$_{20}$ forms, with the nitrogen atom to which it is attached and with a carbon atom of the benzene ring of formula (VI), a heterocycle optionally comprising one or more oxygen atoms and optionally substituted with one or more identical or different C$_1$–C$_4$ alkyl groups;
R21 is a hydrogen or a halogen atom;
R22 and R$_{23}$, which may be identical or different, are chosen from a hydrogen atom and a C$_1$–C$_4$ alkyl radical;
D$_1$ and D$_2$, which may be identical or different, are chosen from a nitrogen atom and a —CH group;
m is equal to 0 or 1;
X$^-$ is an anion; and
E is a group chosen from structures E1 to E9 below:

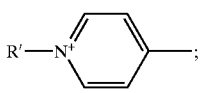
E1

-continued

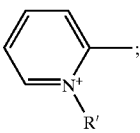
E2

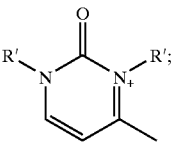
E3

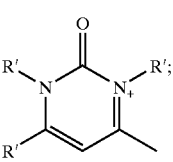
E4

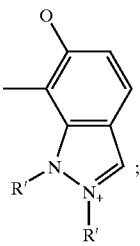
E5

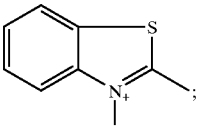
E6

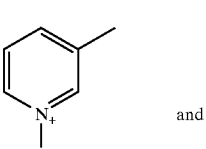
E7 and

E8 and

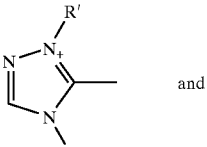

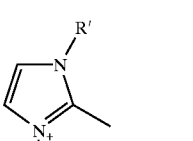
E9 wherein:
R' is a C$_1$–C$_4$ alkyl radical;
with the proviso that:
E can have the structure E9 only when m is equal to 0 and D$_1$ is a nitrogen atom;
with the overall proviso for formula (VI) that:
when R$_{19}$ is an unsubstituted amino group, then D$_1$ and D$_2$ are both —CH, and m is equal to 0;

G—N=N—J (VII)

wherein:
G is a group chosen from structures $G_1$ to $G_3$ below:

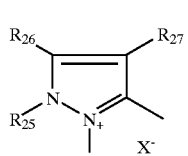

$G_1$

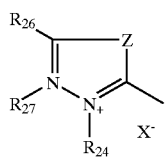

$G_2$

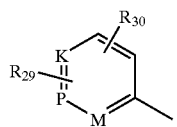

$G_3$ wherein
- $R_{24}$ is chosen from a $C_1$–$C_4$ alkyl radical; a phenyl radical which can be substituted with a $C_1$–$C_4$ alkyl radical; and a halogen atom chosen from chlorine, bromine, iodine and fluorine;
- $R_{25}$ is a $C_1$–$C_4$ alkyl radical or a phenyl radical;
- $R_{26}$ is chosen from a hydrogen atom, a $C_1$–$C_4$ alkyl radical, and a phenyl radical; and $R_{27}$ is chosen from a $C_1$–$C_4$ alkyl radical and a phenyl radical;
- or wherein $R_{26}$ and $R_{27}$ in formula G. together form a benzene ring substituted with one or more identical or different $C_1$–$C_4$ alkyl, $C_1$–$C_4$ alkoxy or $NO_2$ radicals; or further wherein $R_{26}$ and $R_{27}$ in formula G2 together form a benzene ring optionally substituted with one or more identical or different $C_1$–$C_4$ alkyl, $C_1$–$C_4$ alkoxy or $NO_2$ radicals;
- Z is chosen from an oxygen atom, a sulphur atom and a group —$NR_{25}$;
- M, K and P, which may be identical or different, are chosen from —CH, —CR, and —$NR_{28}(X^-)_r$;
- R is $C_1$–$C_4$;
- r is equal to 0 or 1;
- $R_{28}$ is chosen from an atom $O^-$, a $C_1$–$C_4$ alkoxy radical and a $C_1$–$C_4$ alkyl radical;
- $R_{29}$ and $R_{30}$, which may be identical or different, are chosen from a hydrogen atom; a halogen atom chosen from chlorine, bromine, iodine and fluorine; a $C_1$–$C_4$ alkyl radical; a $C_1$–$C_4$ alkoxy radical; and an —$NO_2$ radical;
- $X^-$ is an anion;

with the provisos that:
- if $R_{28}$ is $O^-$, then r is zero;
- if K, P or M is $C_1$–$C_4$—N-alkyl $X^-$, then at least one of $R_{29}$ or $R_{30}$ is other than a hydrogen atom;
- if K is —$NR_{28}(X^-)_r$, then M is equal to P and is chosen from —CH and —CR;
- if M is —$NR_{28}(X^-)_r$, then K is equal to P and is chosen from —CH and —CR;
- if P is —$NR_{28}(X^-)_r$, then K is equal to M and is chosen from —CH and —CR;
- if Z is a sulphur atom and $R_{27}$ is $C_1$–$C_4$ alkyl, then $R_{26}$ is other than a hydrogen atom; and

- if Z is —$NR_{28}$ and $R_{25}$ is $C_1$–$C_4$ alkyl, then at least one of the radicals $R_{24}$, $R_{26}$ or $R_{27}$ of formula $G_2$ is other than a $C_1$–$C_4$ alkyl radical;

and
J is chosen from:
(a) a group of structure $J_1$ below:

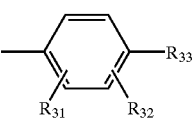

$J_1$ wherein
- $R_{31}$ is chosen from a hydrogen atom; a halogen atom chosen from chlorine, bromine, iodine and fluorine; a $C_1$–$C_4$ alkyl or $C_1$–$C_4$ alkoxy radical; and an —OH, —$NO_2$, —$NHR_{34}$, —$NR_{35}R_{36}$ and $C_1$–$C_4$—NHCO alkyl radical; or wherein $R_{31}$ forms, together with $R_{32}$, a 5- or 6-membered ring optionally comprising one or more identical or different hetero atoms chosen from nitrogen, oxygen and sulphur;
- $R_{32}$ is chosen from a hydrogen atom; a halogen atom chosen from chlorine, bromine, iodine and fluorine; and a $C_1$–$C_4$ alkyl or $C_1$–$C_4$ alkoxy radical; or wherein $R_{32}$ forms, together with $R_{31}$, $R_{33}$ or $R_{34}$, a 5- or 6-membered ring optionally comprising one or more identical or different hetero atoms chosen from nitrogen, oxygen and sulphur;
- $R_{33}$ is chosen from a hydrogen atom; an —OH radical; an —$NHR_{34}$ radical; and an —$NR_{35}R_{36}$ radical;
- $R_{34}$ is chosen from a hydrogen atom; a $C_1$–$C_4$ alkyl radical; a $C_1$–$C_4$ monohydroxyalkyl radical; a $C_2$–$C_4$ polyhydroxyalkyl radical; and a phenyl radical; and
- $R_{35}$ and $R_{36}$, which may be identical or different, are chosen from a $C_1$–$C_4$ alkyl radical; a $C_1$–$C_4$ monohydroxyalkyl radical; and a $C_2$–$C_4$ polyhydroxyalkyl radical; and (b) a 5- or 6-membered nitrogenous heterocyclic group which can comprise one or more additional identical or different hetero atoms and/or one or more carbonyl groups and which can be substituted with one or more identical or different $C_1$–$C_4$ alkyl, amino or phenyl radicals.

29. A process according to claim 28, wherein said keratin fibers are human keratin fibers.

30. A process according to claim 29, wherein said human keratin fibers are hair.

31. A process according to claim 28, wherein J is a 5- or 6-membered nitrogenous heterocyclic group of structure $J_2$ below:

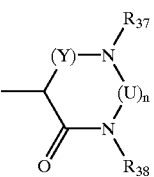

$J_2$ wherein:
- $R_{37}$ and $R_{38}$, which may be identical or different, are chosen from a hydrogen atom, a $C_{13}$–$C_{10}$ alkyl radical and a phenyl radical;

Y is a —CO-radical or a radical

n is equal to 0 or 1; and

U is a —CO— radical when n is equal to 1.

32. A process according to claim 28, wherein the anion X in formulae (I), (II), (III), (IV), (V) and (VI) is chosen from chloride, methylsulphate and acetate.

33. A process according to claim 28, wherein the anion X in the structures $G_1$, $G_2$ and $G_3$ is chosen from chloride, iodide, methyl sulphate, ethyl sulphate, acetate and perchlorate.

34. A process according to claim 28, wherein $R_{14}$ and $R_{15}$ in formula (V) are chosen from a hydrogen atom; a halogen atom chosen from bromine, chlorine, iodine and fluorine; a $C_1$–$C_4$ alkyl or $C_1$–$C_4$ alkoxy radical; and a —CN radical.

35. A process according to claim 28, wherein $R_{19}$ in formula (VI) is chosen from a hydrogen atom; a $C_1$–$C_4$ alkoxy radical; a halogen atom chosen from bromine, chlorine, iodine and fluorine; and an amino radical.

36. A process according to claim 28, wherein $R_{21}$ in formula (VI) is chosen from hydrogen, bromine, chlorine, iodine and fluorine atoms.

37. A process according to claim 28, wherein said dye composition is applied to keratin fibers, and after said composition is allowed to act on said fibers for a period which is sufficient to develop the desired dyeing results, said fibres are rinsed, optionally washed with shampoo and rinsed again, and dried.

38. A process according to claim 28, wherein said dye composition is applied to keratin fibers, and after said composition is allowed to act on said fibers for a period which is sufficient to develop the desired dyeing results, said fibers are dried without final rinsing.

39. A multi-compartment dyeing device, comprising a first compartment and a second compartment, wherein said first compartment contains at least one cationic dye of formulae (I) to (III) defined below, and wherein said second compartment contains at least one cationic dye of formulae (IV) to (VII) defined below, wherein said first and second compartments do not contain an oxidizing agent:

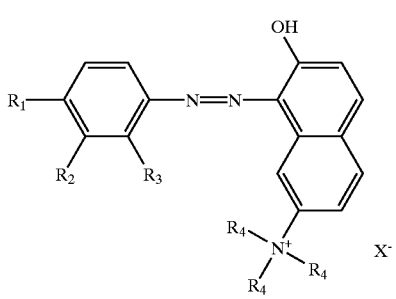

(I)

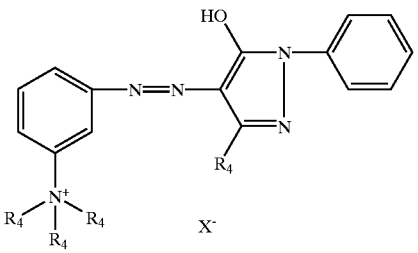

(II)

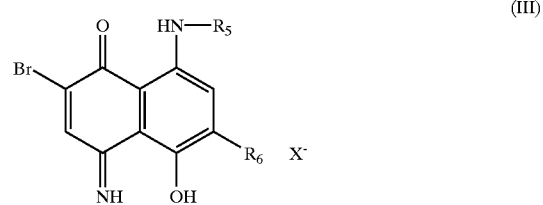

(III)

wherein:

$R_1$ is a hydrogen atom or an amino radical;

$R_2$ is a hydrogen atom or a nitro group;

$R_3$ is a hydrogen atom, a nitro group or a $C_1$–$C_4$ alkoxy radical;

$R_4$ is a $C_1$–$C_4$ alkyl radical;

$R_5$ is a hydrogen atom or a para-tri($C_1$–$C_4$) alkylammoniophenyl group;

$R_6$ is a bromine atom or an NH-para-tri-($C_1$–$C_4$) alkylammoniophenyl group; and $X^-$ is an anion

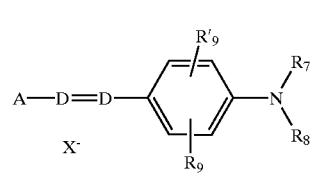

(IV)

wherein:

D is a nitrogen atom or a —CH group, $R_7$ and $R_8$, which may be identical or different, are chosen from a hydrogen atom;

a 4'-aminophenyl radical; and a $C_1$–$C_4$ alkyl radical which can be substituted with a —CN, —OH or —NH$_2$ radical or which can form, with the nitrogen atom to which it is attached and with a carbon atom of the benzene ring of formula (IV), a heterocycle optionally comprising one or more oxygen atoms or additional nitrogen atoms, said heterocycle being optionally substituted with one or more identical or different $C_1$–$C_4$ alkyl radicals;

$R_9$ and $R'_9$, which may be identical or different, are chosen from a hydrogen atom; a halogen atom chosen from chlorine, bromine, iodine and fluorine; a cyano radical; a $C_1$–$C_4$ alkyl radical; a $C_1$–$C_4$ alkoxy radical; and an acetyloxy radical;

$X^-$ is an anion; and

A is a group chosen from structures A1 to A19 below:
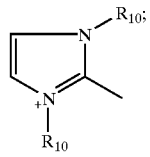
A1
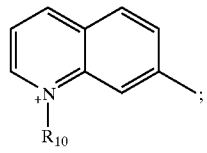
A2
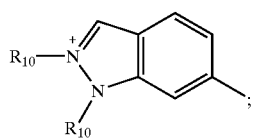
A3
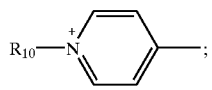
A4
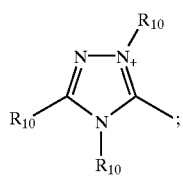
A5
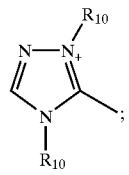
A6
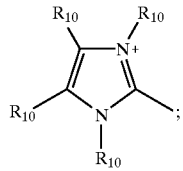
A7
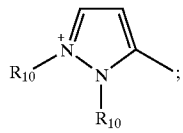
A8
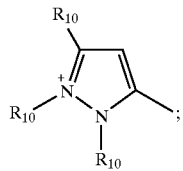
A9
-continued
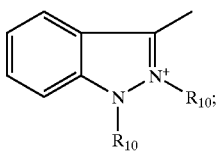
A10
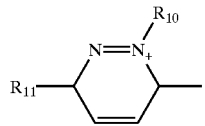
A11
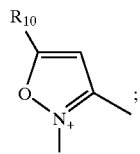
A12
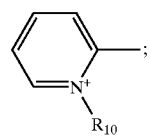
A13
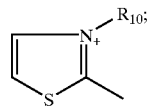
A14
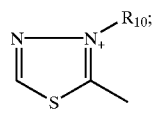
A15
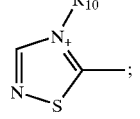
A16
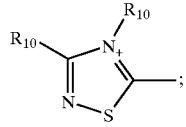
A17
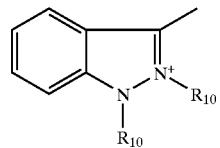
A18 and
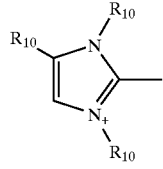
A19
wherein:
$R_{10}$ is a $C_1$–$C_4$ alkyl radical which can be substituted with a hydroxyl radical; and $R_{11}$ is a $C_1$–$C_4$ alkoxy radical;

with the overall provisos for formula (IV) that:

(i) when D is —CH, A is $A_4$ or $A_{13}$, and $R_9$ is other than an alkoxy radical, then at least one of $R_7$ and $R_8$ is not a hydrogen atom; and (ii) when D is a nitrogen atom, and A is $A_6$, then at least one of $R_7$ and $R_8$ is not a methyl radical;

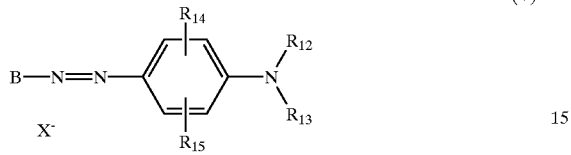
(V)

wherein:

$R_{12}$ is a hydrogen atom or a $C_1$–$C_4$ alkyl radical;

$R_{13}$ is chosen from a hydrogen atom; an alkyl radical which can be substituted with a —CN radical or with an amino group; and a 4'-aminophenyl radical; or wherein $R_{13}$ forms, together with $R_{12}$ and the nitrogen atom to which they are attached, a heterocycle optionally containing one or more oxygen atoms and/or additional nitrogen atoms, said heterocycle being optionally substituted with a $C_1$–$C_4$ alkyl radical;

$R_{14}$ and $R_{15}$, which may be identical or different, are chosen from a hydrogen atom, a halogen atom; a $C_1$–$C_4$ alkyl radical; a $C_1$–$C_4$ alkoxy radical; and a —CN radical;

$X^-$ is an anion; and

B is a group chosen from structures B1 to B6 below:

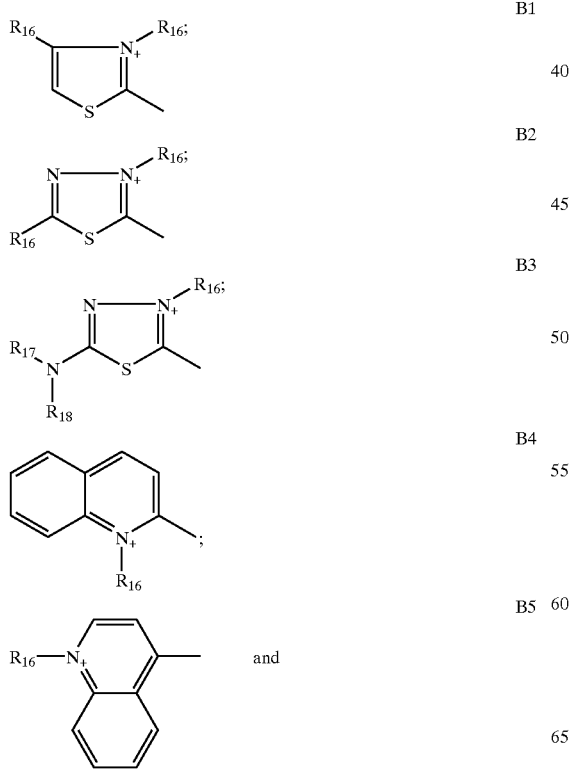

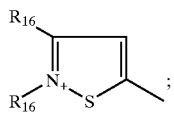
B6 wherein:

$R_{16}$ is a $C_1$–$C_4$ alkyl radical; and $R_{17}$ and $R_{18}$, which may be identical or different, are chosen from a hydrogen atom and a $C_1$–$C_4$ alkyl radical;

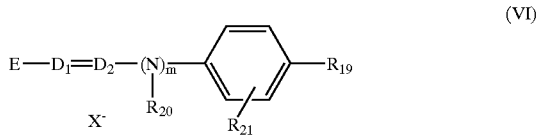
(VI)

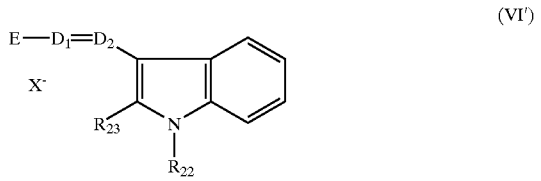
(VI')

wherein:

$R_{19}$ is chosen from a hydrogen atom; a $C_1$–$C_4$ alkoxy radical; a halogen atom; and an amino radical;

$R_{20}$ is a hydrogen atom or a $C_1$–$C_4$ alkyl radical; or wherein $R_{20}$ forms, with the to nitrogen atom to which it is attached and with a carbon atom of the benzene ring of formula (VI), a heterocycle optionally comprising one or more oxygen atoms and optionally substituted with one or more identical or different $C_1$–$C_4$ alkyl groups;

$R_{21}$ is a hydrogen or a halogen atom;

$R_{22}$ and $R_{23}$, which may be identical or different, are chosen from a hydrogen atom and a $C_1$–$C_4$ alkyl radical;

$D_1$ and $D_2$, which may be identical or different, are chosen from a nitrogen atom and a —CH group;

m is equal to 0 or 1;

$X^-$ is an anion; and

E is a group chosen from structures E1 to E9 below:

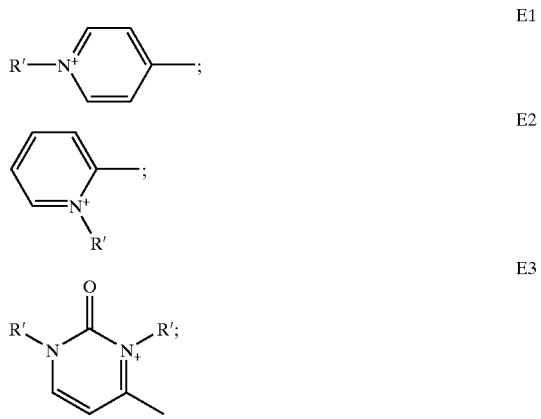

-continued

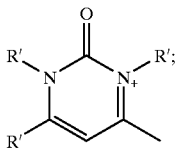  E4

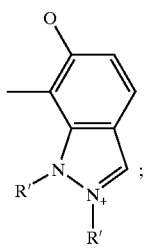  E5

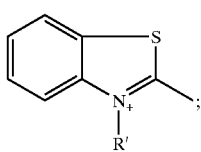  E6

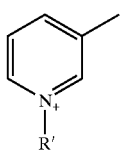 and  E7

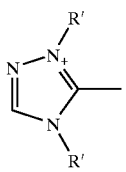 and  E8

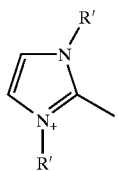  E9 wherein:
R' is a $C_1$–$C_4$ alkyl radical;
with the proviso that:
E can have the structure E9 only when m is equal to 0 and $D_1$ is a nitrogen atom;
with the overall proviso for formula (VI) that:
when $R_{19}$ is an unsubstituted amino group, then $D_1$ and $D_2$ are both —CH, and m is equal to 0;

 (VI)

wherein:

G is a group chosen from structures $G_1$ to $G_3$ below:

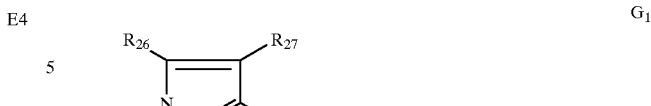  $G_1$

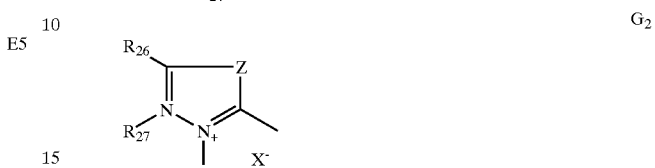  $G_2$

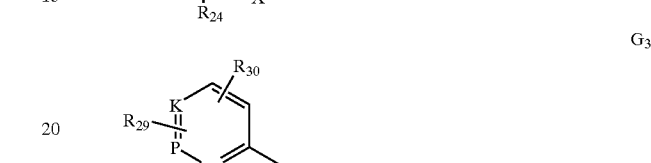  $G_3$ wherein
$R_{24}$ is chosen from a $C_1$–$C_4$ alkyl radical; a phenyl radical which can be substituted with a $C_1$–$C_4$ alkyl radical; and a halogen atom chosen from chlorine, bromine, iodine and fluorine;
$R_{25}$ is a $C_1$–$C_4$ alkyl radical or a phenyl radical;
$R_{26}$ is chosen from a hydrogen atom, a $C_1$–$C_4$ alkyl radical, and a phenyl radical; and $R_{27}$ is chosen from a $C_1$–$C_4$ alkyl radical and a phenyl radical; or wherein $R_{26}$ and $R_{27}$ in formula $G_1$ together form a benzene ring substituted with one or more identical or different $C_1$–$C_4$ alkyl, $C_1$–$C_4$ alkoxy or $NO_2$ radicals; or further wherein $R_{26}$ and $R_{27}$ in formula $G_2$ together form a benzene ring optionally substituted with one or more identical or different $C_1$–$C_4$ alkyl, $C_1$–$C_4$ alkoxy or $NO_2$ radicals;
Z is chosen from an oxygen atom, a sulphur atom and a group —$NR_{25}$;
M, K and P, which may be identical or different, are chosen from —CH, —CR, and —$NR_{28}(X^-)_r$;
R is $C_1$–$C_4$;
r is equal to 0 or 1;
$R_{28}$ is chosen from an atom $O^-$, a $C_1$–$C_4$ alkoxy radical and a $C_1$–$C_4$ alkyl radical;
$R_{29}$ and $R_{30}$, which may be identical or different, are chosen from a hydrogen atom; a halogen atom chosen from chlorine, bromine, iodine and fluorine; a $C_1$–$C_4$ alkyl radical; a $C_1$–$C_4$ alkoxy radical; and an —$NO_2$ radical;
$X^-$ is an anion;
with the provisos that:
if $R_{28}$ is $O^-$, then r is zero;
if K, P or M is $C_1$–$C_4$—N-alkyl $X^-$, then at least one of $R_{29}$ or $R_{30}$ is other than a hydrogen atom;
if K is —$NR_{28}(X^-)_r$, then M is equal to P and is chosen from —CH and —CR;
if M is —$NR_{28}(X^-)_r$, then K is equal to P and is chosen from —CH and —CR;
if P is —$NR_{28}(X^-)_r$, then K is equal to M and is chosen from —CH and —CR;
if Z is a sulphur atom and $R_{27}$ is $C_1$–$C_4$ alkyl, then $R_{26}$ is other than a hydrogen atom; and if Z is —NR$_{28}$ and R$_{25}$ is C$_1$–C$_4$ alkyl, then at least one of the radicals R$_{24}$, R$_{26}$ or R$_{27}$ of formula G$_2$ is other than a C$_1$–C$_4$ alkyl radical;
and
J is chosen from:
(a) a group of structure J$_1$ below:

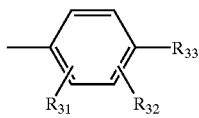

J$_1$ wherein
R$_{31}$ is chosen from a hydrogen atom; a halogen atom chosen from chlorine, bromine, iodine and fluorine; a C$_1$–C$_4$ alkyl or C$_1$–C$_4$ alkoxy radical; and an —OH, —NO$_2$, —NHR$_{34}$,— NR$_{35}$R$_{36}$ and C$_1$–C$_4$—NHCO alkyl radical; or wherein R$_{31}$ forms, together with R$_{32}$, a 5- or 6-membered ring optionally comprising one or more identical or different hetero atoms chosen from nitrogen, oxygen and sulphur;

R$_{32}$ is chosen from a hydrogen atom; a halogen atom chosen from chlorine, bromine, iodine and fluorine; and a C$_1$–C$_4$ alkyl or C$_1$–C$_4$ alkoxy radical; or wherein R$_{32}$ forms, together with R$_{31}$, R$_{33}$ or R$_{34,}$ a 5- or 6-membered ring optionally comprising one or more identical or different hetero atoms chosen from nitrogen, oxygen and sulphur;

R$_{33}$ is chosen from a hydrogen atom; an —OH radical; an —NHR$_{34}$ radical; and an —NR$_{35}$R$_{36}$ radical;

R$_{34}$ is chosen from a hydrogen atom; a C$_1$–C$_4$ alkyl radical; a C$_1$–C$_4$ monohydroxyalkyl radical; a C$_2$–C$_4$ polyhydroxyalkyl radical; and a phenyl radical; and R$_{35}$ and R$_{36}$, which may be identical or different, are chosen from a C$_1$–C$_4$ alkyl radical; a C$_1$–C$_4$ monohydroxyalkyl radical; and a C$_2$–C$_4$ polyhydroxyalkyl radical; and (b) a 5- or 6-membered nitrogenous heterocyclic group which can comprise one or more additional identical or different hetero atoms and/or one or more carbonyl groups and which can be substituted with one or more identical or different C$_1$–C$_4$ alkyl amino or phenyl radicals.

40. A multi-compartment dyeing device according to claim 39, wherein J is a 5- or 6-membered nitrogenous heterocyclic group of structure J$_2$ below:

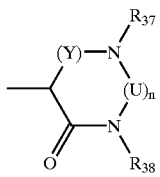

J$_2$ wherein:

R$_{37}$ and R$_{38}$ which may be identical or different, are chosen from a hydrogen atom, a C$_{13}$–C$_{10}$ alkyl radical and a phenyl radical;

Y is a —CO— radical or a radical

n is equal to 0 or 1; and

U is a —CO— radical when n is equal to 1.

41. A multi-compartment dyeing device according to claim 39, wherein the anion X in formulae (I), (I), (III), (IV), (V) and (VI) is chosen from chloride, methylsulphate and acetate.

42. A multi-compartment dyeing device according to claim 39, wherein the anion X$^-$ in the structures G$_1$, G$_2$ and G$_3$ is chosen from chloride, iodide, methyl sulphate, ethyl sulphate, acetate and perchlorate.

43. A multi-compartment dyeing device according to claim 39, wherein R$_{14}$ and R$_{14}$ in formula (V) are chosen from a hydrogen atom; a halogen atom chosen from bromine, chlorine, iodine and fluorine; a C$_1$–C$_4$ alkyl or C$_1$–C$_4$ alkoxy radical; and a —CN radical.

44. A multi-compartment dyeing device according to claim 39, wherein R$_{19}$ in formula (VI) is chosen from a hydrogen atom; a C$_1$–C$_4$ alkoxy radical; a halogen atom chosen from bromine, chlorine, iodine and fluorine; and an amino radical.

45. A multi-compartment dyeing device according to claim 39, wherein R$_{21}$ in formula (VI) is chosen from hydrogen, bromine, chlorine, iodine and fluorine atoms.

46. A multi-compartment dyeing device, comprising a first compartment and a second compartment, wherein said first compartment contains a pulverulent composition comprising the combination of at least one cationic dye of formulae (I) to (II) and at least one dye of formulae (IV) to (VII), and wherein said second compartment contains an aqueous composition, wherein said aqueous composition is a vehicle for dyeing keratinous fibers, and said first and second compartments do not contain an oxidizing agent:

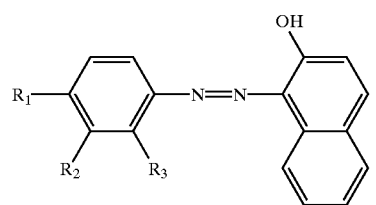

(I)

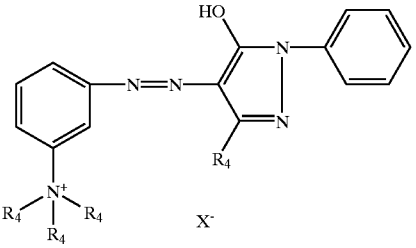

(II)

-continued

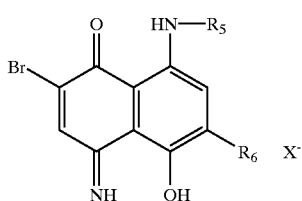
(III)

wherein:

R₁ is a hydrogen atom or an amino radical;

R₂ is a hydrogen atom or a nitro group;

R₃ is a hydrogen atom, a nitro group or a $C_1$–$C_4$ alkoxy radical;

R₄ is a $C_1$–$C_4$ alkyl radical;

R₅ is a hydrogen atom or a para-tri($C_1$–$C_4$) alkylammoniophenyl group;

R₆ is a bromine atom or an NH-para-tri-($C_1$–$C_4$) alkylammoniophenyl group; and X⁻ is an anion

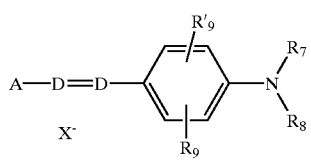
(IV)

wherein:

D is a nitrogen atom or a —CH group,

R₇ and R₈, which may be identical or different, are chosen from a hydrogen atom; a 4'-aminophenyl radical; and a $C_1$–$C_4$ alkyl radical which can be substituted with a —CN, —OH or —NH₂ radical or which can form, with the nitrogen atom to which it is attached and with a carbon atom of the benzene ring of formula (IV), a heterocycle optionally comprising one or more oxygen atoms or additional nitrogen atoms, said heterocycle being optionally substituted with one or more identical or different $C_1$–$C_4$ alkyl radicals;

R₉ and R'₉, which may be identical or different, are chosen from a hydrogen atom; a halogen atom chosen from chlorine, bromine, iodine and fluorine; a cyano radical; a $C_1$–$C_4$ alkyl radical; a $C_1$–$C_4$ alkoxy radical; and an acetyloxy radical;

X⁻ is an anion; and

A is a group chosen from structures A1 to A19 below:

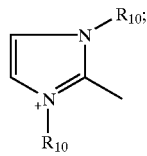
A₁

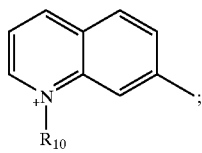
A₂

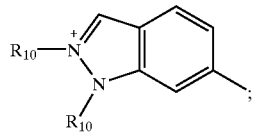
A₃

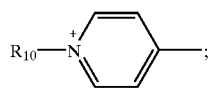
A₄

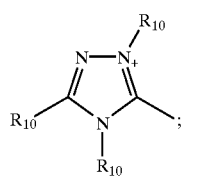
A₅

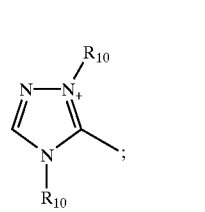
A₆

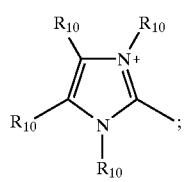
A₇

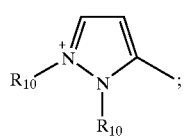
A₈

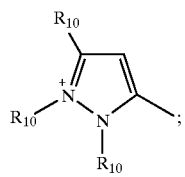
A₉

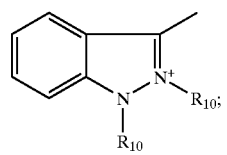
A₁₀

-continued

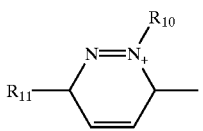
A₁₁

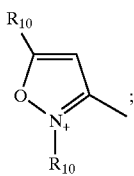
A₁₂

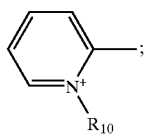
A₁₃

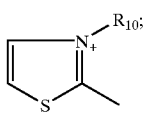
A₁₄

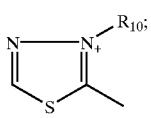
A₁₅

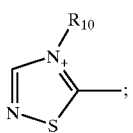
A₁₆

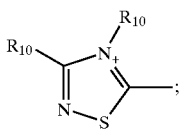
A₁₇

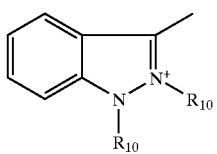
A₁₈ and

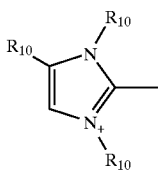
A₁₉ wherein:
$R_{10}$ is a $C_1$–$C_4$ alkyl radical which can be substituted with a hydroxyl radical; and
$R_{11}$ is a $C_1$–$C_4$ alkoxy radical;
with the overall provisos for formula (IV) that:
(i) when D is —CH, A is $A_4$ or $A_{13}$, and $R_9$ is other than an alkoxy radical, then at least one of $R_7$ and $R_8$ is not a hydrogen atom; and
(ii) when D is a nitrogen atom, and A is $A_6$, then at least one of $R_7$ and $R_8$ is not a methyl radical;

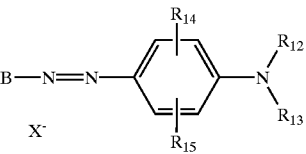
(V)

wherein:
$R_{12}$ is a hydrogen atom or a $C_1$–$C_4$ alkyl radical;
$R_{13}$ is chosen from a hydrogen atom; an alkyl radical which can be substituted with a —CN radical or with an amino group; and a 4'-aminophenyl radical; or wherein $R_{13}$ forms, together with $R_{12}$ and the nitrogen atom to which they are attached, a heterocycle optionally containing one or more oxygen atoms and/or additional nitrogen atoms, said heterocycle being optionally substituted with a $C_1$–$C_4$ alkyl radical;
$R_{14}$ and $R_{15}$, which may be identical or different, are chosen from a hydrogen atom, a halogen atom; a $C_1$–$C_4$ alkyl radical; a $C_1$–$C_4$ alkoxy radical; and a —CN radical;
X⁻ is an anion; and
B is a group chosen from structures B1 to B6 below:

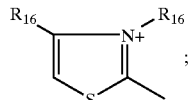
B1

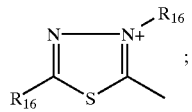
B2

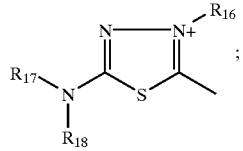
B3

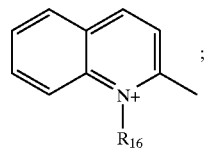
B4

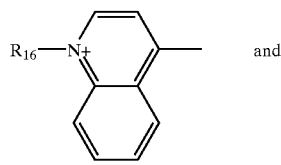
B5 and

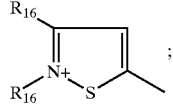
B6 wherein:
$R_{16}$ is a $C_1$–$C_4$ alkyl radical; and
$R_{17}$ and $R_{18}$, which may be identical or different, are chosen from a hydrogen atom and a $C_1$–$C_4$ alkyl radical;

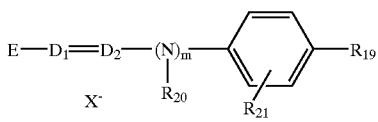 (VI)

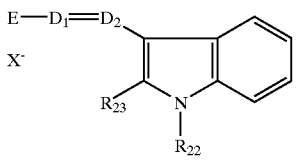 (VI')

wherein:

- $R_{19}$ is chosen from a hydrogen atom; a $C_1$–$C_4$ alkoxy radical; a halogen atom; and an amino radical;
- $R_{20}$ is a hydrogen atom or a $C_1$–$C_4$ alkyl radical; or wherein $R_{20}$ forms, with the nitrogen atom to which it is attached and with a carbon atom of the benzene ring of formula (VI), a heterocycle optionally comprising one or more oxygen atoms and optionally substituted with one or more identical or different $C_1$–$C_4$ alkyl groups;
- $R_{21}$ is a hydrogen or a halogen atom;
- $R_{22}$ and $R_{23}$, which may be identical or different, are chosen from a hydrogen atom and a $C_1$–$C_4$ alkyl radical;
- $D_1$ and $D_2$, which may be identical or different, are chosen from a nitrogen atom and a —CH group;
- m is equal to 0 or 1;
- $X^-$ is an anion; and
- E is a group chosen from structures E1 to E9 below:

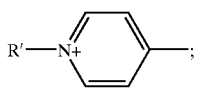 E1

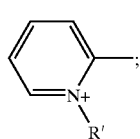 E2

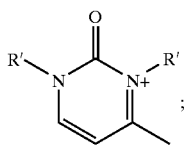 E3

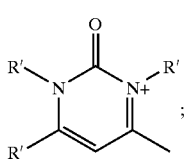 E4

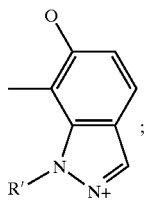 E5

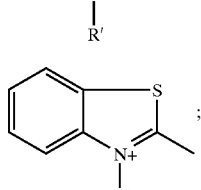 E6

 E7 and

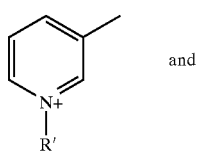 E8 and

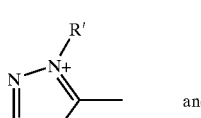 E9

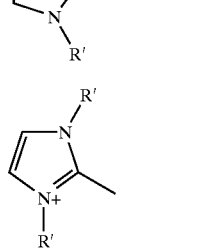

wherein:
R' is a $C_1$–$C_4$ alkyl radical;
with the proviso that:
E can have the structure E9 only when m is equal to 0 and $D_1$ is a nitrogen atom;
with the overall proviso for formula (VI) that:
when $R_{19}$ is an unsubstituted amino group, then $D_1$ and $D_2$ are both —CH, and m is equal to 0;

 (VII)

G—N=N—J wherein:
G is a group chosen from structures $G_1$ to $G_3$ below:

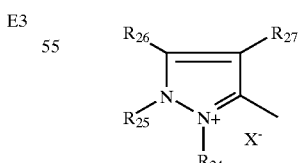 $G_1$

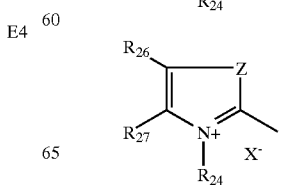 $G_2$

-continued

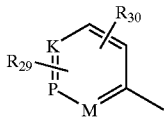

G₃ wherein
- R₂₄ is chosen from a $C_1$–$C_4$ alkyl radical; a phenyl radical which can be substituted with a $C_1$–$C_4$ alkyl radical; and a halogen atom chosen from chlorine, bromine, iodine and fluorine;
- R₂₅ is a $C_1$–$C_4$ alkyl radical or a phenyl radical;
- R₂₆ is chosen from a hydrogen atom, a $C_1$–$C_4$ alkyl radical, and a phenyl radical; and R₂₇ is chosen from a $C_1$–$C_4$ alkyl radical and a phenyl radical; or wherein R₂₆ and R₂₇ in formula G₁ together form a benzene ring substituted with one or more identical or different $C_1$–$C_4$ alkyl, $C_1$–$C_4$ alkoxy $NO_2$ radicals; or further wherein R₂₆ and R₂₇ in formula G₂ together form a benzene ring optionally substituted with one or more identical or different $C_1$–$C_4$ alkyl, $C_1$–$C_4$ alkoxy or $NO_2$ radicals;
- Z is chosen from an oxygen atom, a sulphur atom and a group —NR₂₅;
- M, K and P, which may be identical or different, are chosen from —CH, —CR, and —NR₂₈(X⁻)ᵣ;
- R is $C_1$–$C_4$;
- R is equal to 0 or 1;
- R₂₈ is chosen from an atom O⁻, a $C_1$–$C_4$ alkoxy radical and a $C_1$–$C_4$ alkyl radical;
- R₂₉ and R₃₀, which may be identical or different, are chosen from a hydrogen atom; a halogen atom chosen from chlorine, bromine, iodine and fluorine; a $C_1$–$C_4$ alkyl radical; a $C_1$–$C_4$ alkoxy radical; and an —NO₂ radical;
- X⁻ is an anion;

with the provisos that:

if R₂₈ is O⁻, then r is zero;
if K, P or M is $C_1$–$C_4$—N-alkyl X⁻, then at least one of R₂₉ or R₃₀ is other than a hydrogen atom;
if K is —NR₂₈(X⁻)ᵣ, then M is equal to P and is chosen from —CH and —CR;
if M is —NR₂₈(X⁻)ᵣ, then K is equal to P and is chosen from —CH and —CR;
if P is —NR₂₈(X⁻)ᵣ, then K is equal to M and is chosen from —CH and —CR;
if Z is a sulphur atom and R₂₇ is $C_1$–$C_4$ alkyl, then R₂₆ is other than a hydrogen atom; and
if Z is —NR₂₈ and R₂₅ is $C_1$–$C_4$ alkyl, then at least one of the radicals R₂₄, R₂₆ or R₂₇ of formula G₂ is other than a $C_1$–$C_4$ alkyl radical;

and

J is chosen from:

(a) a group of structure J₁ below:

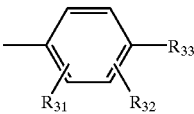

J₁ wherein
- R₃₁ is chosen from a hydrogen atom; a halogen atom chosen from chlorine, bromine, iodine and fluorine; a $C_1$–$C_4$ alkyl or $C_1$–$C_4$ alkoxy radical; and an —OH, —NO₂, —NHR₃₄, —NR₃₅R₃₆ and $C_1$–$C_4$—NHCO alkyl radical; or wherein R₃₁ forms, together with R₃₂, a 5- or 6-membered ring optionally comprising one or more identical or different hetero atoms chosen from nitrogen, oxygen and sulphur;
- R₃₂ is chosen from a hydrogen atom; a halogen atom chosen from chlorine, bromine, iodine and fluorine; and a $C_1$–$C_4$ alkyl or $C_1$–$C_4$ alkoxy radical; or wherein R₃₂ forms, together with R₃₁, R₃₃ or R₃₄, a 5- or 6-membered ring optionally comprising one or more identical or different hetero atoms chosen from nitrogen, oxygen and sulphur;
- R₃₃ is chosen from a hydrogen atom; an —OH radical; an —NHR₃₄ radical; and an —NR₃₅R₃₆ radical;
- R₃₄ is chosen from a hydrogen atom; a $C_1$–$C_4$ alkyl radical; a $C_1$–$C_4$ monohydroxyalkyl radical; a $C_2$–$C_4$ polyhydroxyalkyl radical; and a phenyl radical; and
- R₃₅ and R₃₆, which may be identical or different, are chosen from a $C_1$–$C_4$ alkyl radical; a $C_1$–$C_4$ monohydroxyalkyl radical; and a $C_2$–$C_4$ polyhydroxyalkyl radical; and (b) a 5- or 6-membered nitrogenous heterocyclic group which can comprise one or more additional identical or different hetero atoms and/or one or more carbonyl groups and which can be substituted with one or more identical or different $C_1$–$C_4$ alkyl, amino or phenyl radicals.

47. A multi-compartment dyeing device according to claim 46, wherein J is a 5- or 6-membered nitrogenous heterocyclic group of structure J₂ below:

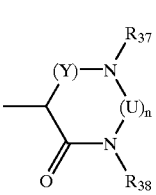

J₂ wherein:

R₃₇ and R₃₈, which may be identical or different, are chosen from a hydrogen atom, a $C_{13}$–$C_{10}$ alkyl radical and a phenyl radical;

Y is a —CO— radical or a radical

n is equal to 0 or 1; and

U is a —CO— radical when n is equal to 1.

48. A multi-compartment dyeing device according to claim 46, wherein the anion X in formulae (I), (II), (III), (IV), (V) and (VI) is chosen from chloride, methylsulphate and acetate.

49. A multi-compartment dyeing device according to claim 46, wherein the anion $X^-$ in the structures $G_1$, $G_2$ and $G_3$ is chosen from chloride, iodide, methyl sulphate, ethyl sulphate, acetate and perchlorate.

50. A multi-compartment dyeing device according to claim 46, wherein $R_{14}$ and $R_{15}$ in formula (V) are chosen from a hydrogen atom; a halogen atom chosen from bromine, chlorine, iodine and fluorine; a $C_1$–$C_4$ alkyl or $C_1$–$C_4$ alkoxy radical; and a —CN radical.

51. A multi-compartment dyeing device according to claim 46, wherein $R_{19}$ in formula (VI) is chosen from a hydrogen atom; a $C_1$–$C_4$ alkoxy radical; a halogen atom chosen from bromine, chlorine, iodine and fluorine; and an amino radical.

52. A multi-compartment dyeing device according to claim 46, wherein $R_{21}$ in formula (VI) is chosen from hydrogen, bromine, chlorine, iodine and fluorine atoms.

* * * * *

UNITED STATES PATENT AND TRADEMARK OFFICE
CERTIFICATE OF CORRECTION

PATENT NO.    : 6,432,146 B1
DATED         : August 13, 2002
INVENTOR(S)   : Christine Rondeau It is certified that error appears in the above-identified patent and that said Letters Patent is hereby corrected as shown below:

Column 33,
Line 60, after "claimed" delete the period.

Column 40,
Line 28, "radical:" should read -- radical; --.
Line 33, "N$_2$" should read -- NO$_2$ --.
Line 37, "N$_{o2}$" should read -- NO$_2$ --.
Line 43, "0or 1" should read -- 0 or 1 --.

Column 42,
Line 22, "Rlg" should read -- R$_{19}$ --.

Column 55, structure (VII23),
Lines 5 and 8, both occurrences of "C$_2$H$_5$" should read -- CH$_3$ --.

Column 57, structure (VII44),
Line 55, "O$^-$" should read -- OCH$_3$ --.

Column 61, structure (VII71),
Line 29, "H" should read -- CH$_3$ --.

Column 66,
Line 47, "X is" should read -- X$^-$ is --.

Column 67,
Line 24, "R$_8$" should read -- R$_{18}$ --.
Line 52, "R21" should read -- R$_{21}$ --.
Line 53, "R22" should read -- R$_{22}$ --.

Column 69, structure G$_2$,
Lines 11-17, 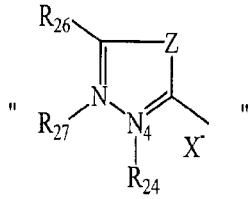 should read 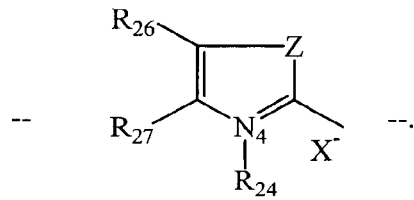 --.

UNITED STATES PATENT AND TRADEMARK OFFICE
CERTIFICATE OF CORRECTION

PATENT NO. : 6,432,146 B1
DATED : August 13, 2002
INVENTOR(S) : Christine Rondeau It is certified that error appears in the above-identified patent and that said Letters Patent is hereby corrected as shown below:

Column 69,
Line 34, "G." should read -- $G_1$ --.
Line 37, "$R_{26}$and $R_{27}$in" should read -- $R_{26}$ and $R_{27}$ in --.
Line 37, "G2" should read -- $G_2$ --.

Column 71,
Lines 12 and 15, "X" should read -- $X^-$ --.
Line 33, after "with the" delete "to".

Column 76,
Line 33, after "with the" delete "to".

Column 77,
Line 64, "(VI)" should read -- (VII) --.

Column 78, structure $G_2$,
Lines 10-16,             should read

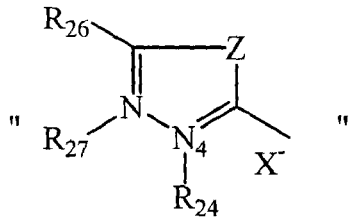   --   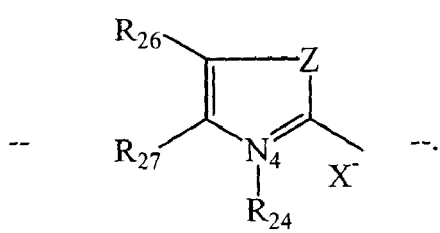   --.

Column 79,
Lines 19-20, "-$NHR_{34}$,- $NR_{35}R_{36}$" should read -- $NHR_{34}$, -$NR_{35}R_{36}$ --.
Line 65, after "$R_{38}$" insert a comma.

Column 80,
Line 8, "0or 1" should read -- 0 or 1 --.
Line 12, "X in" should read -- $X^-$ in --.
Line 12, the second occurrence of "(I)" should read -- (II) --.
Line 21, the second occurrence of "$R_{14}$" should read -- $R_{15}$ --.
Line 39, "(II)" should read -- (III) --.

UNITED STATES PATENT AND TRADEMARK OFFICE
CERTIFICATE OF CORRECTION

PATENT NO. : 6,432,146 B1
DATED : August 13, 2002
INVENTOR(S) : Christine Rondeau It is certified that error appears in the above-identified patent and that said Letters Patent is hereby corrected as shown below:

Column 83,
Line 66, "A6" should read -- $A_6$ --.

Column 87,
Line 22, before "$NO_2$" insert -- or --.

Column 89,
Line 11, "X in" should read -- $X^-$ in --.

Signed and Sealed this

Eleventh Day of February, 2003

JAMES E. ROGAN
*Director of the United States Patent and Trademark Office*